US012329471B2

(12) United States Patent
Balter et al.

(10) Patent No.: US 12,329,471 B2
(45) Date of Patent: Jun. 17, 2025

(54) SURGICAL ROBOTIC SYSTEM USER INTERFACES

(71) Applicant: Covidien LP, Mansfield, MA (US)

(72) Inventors: Max L. Balter, Boston, MA (US);
Diana Chen, Braintree, MA (US);
Walter Schoen, Cambridge, MA (US);
William J. Peine, Ashland, MA (US);
Jared Farlow, Los Angeles, CA (US)

(73) Assignee: Covidien LP, Mansfield, MA (US)

( * ) Notice: Subject to any disclaimer, the term of this patent is extended or adjusted under 35 U.S.C. 154(b) by 990 days.

(21) Appl. No.: 17/427,679

(22) PCT Filed: May 26, 2021

(86) PCT No.: PCT/US2021/034125
§ 371 (c)(1),
(2) Date: Aug. 2, 2021

(87) PCT Pub. No.: WO2021/247294
PCT Pub. Date: Dec. 9, 2021

(65) Prior Publication Data
US 2023/0157772 A1    May 25, 2023

Related U.S. Application Data

(60) Provisional application No. 63/033,969, filed on Jun. 3, 2020.

(51) Int. Cl.
*A61B 34/30* (2016.01)
*A61B 34/00* (2016.01)
(Continued)

(52) U.S. Cl.
CPC .............. *A61B 34/30* (2016.02); *A61B 34/25* (2016.02); *A61B 50/13* (2016.02); *B25J 5/007* (2013.01);
(Continued)

(58) Field of Classification Search
CPC ......... A61B 34/30; A61B 34/25; A61B 50/13; A61B 2034/2059; A61B 2090/067;
(Continued)

(56) References Cited

U.S. PATENT DOCUMENTS 11,666,392 B2 *   6/2023   Kim ..................... A61B 34/20
                                                            700/264
2010/0204713 A1 * 8/2010   Ruiz Morales .......... B25J 9/041
                                                            606/130

(Continued)

FOREIGN PATENT DOCUMENTS

WO    2019204013 A1    10/2019
WO    2020214193 A1    10/2020
WO    2021030651 A1    2/2021

OTHER PUBLICATIONS

International Search Report dated Nov. 5, 2021 issued in corresponding PCT Appln. No. PCT/US2021/034125.

*Primary Examiner* — Sze-Hon Kong
(74) *Attorney, Agent, or Firm* — Carter, DeLuca & Farrell LLP

(57) ABSTRACT

A surgical robotic system includes: a surgical table; a plurality of movable carts being oriented toward the surgical table, each of which includes a robotic arm, and an alignment unit configured to determine an orientation of the movable cart and the robotic arm relative to the surgical (Continued)

table; and a computer coupled to each of the plurality of movable carts and configured to calculate a yaw angle for each of the plurality of movable carts.

15 Claims, 20 Drawing Sheets

(51) Int. Cl.
*A61B 50/13* (2016.01)
*B25J 5/00* (2006.01)
*B25J 9/00* (2006.01)
*B25J 9/16* (2006.01)
*A61B 34/20* (2016.01)
*A61B 90/00* (2016.01)

(52) U.S. Cl.
CPC ........... *B25J 9/0084* (2013.01); *B25J 9/1628* (2013.01); *A61B 2034/2059* (2016.02); *A61B 2090/067* (2016.02)

(58) Field of Classification Search
CPC .. A61B 2017/00725; A61B 2034/2055; A61B 34/37; A61B 2034/2074; A61B 90/37; A61B 90/60; A61B 90/92; A61B 90/08; A61B 2090/0803; A61B 2090/0804; A61B 2090/0807; A61B 2090/0811; B25J 5/007; B25J 9/0084; B25J 9/1628; B25J 9/1671; A61G 12/001
See application file for complete search history.

(56) References Cited

U.S. PATENT DOCUMENTS

| | | | |
|---|---|---|---|
| 2014/0135790 A1* | 5/2014 | Fenster | A61B 90/11 606/130 |
| 2014/0276855 A1* | 9/2014 | de la Barrera | A61B 17/154 705/2 |
| 2015/0100066 A1* | 4/2015 | Kostrzewski | A61B 34/30 606/130 |
| 2017/0079730 A1 | 3/2017 | Azizian et al. | |
| 2018/0289427 A1* | 10/2018 | Griffiths | A61B 34/32 |
| 2018/0344421 A1* | 12/2018 | Cagle | A61B 90/50 |
| 2019/0069962 A1* | 3/2019 | Tabandeh | A61B 34/25 |
| 2019/0320995 A1* | 10/2019 | Amiri | A61B 6/4405 |
| 2019/0321115 A1* | 10/2019 | Anderson | A61B 17/3423 |
| 2021/0154837 A1* | 5/2021 | Kishida | B25J 9/106 |
| 2024/0099790 A1* | 3/2024 | Johnson | G06F 3/04845 |

* cited by examiner

SURGICAL ROBOTIC SYSTEM USER INTERFACES

CROSS-REFERENCE TO RELATED APPLICATIONS

The present application is a U.S. National Phase Application of International PCT Application Serial No. PCT/US2021/034125 under 35 U.S.C. § 371 (a), filed on May 26, 2021, which claims the benefit of and priority to U.S. Provisional Application Ser. No. 63/033,969, filed on Jun. 3, 2020. The entire contents of each of the foregoing applications are incorporated by reference herein.

BACKGROUND

1. Technical Field

The present disclosure generally relates to a surgical robotic system having one or more modular arm carts each of which supports a robotic arm and a surgical console for controlling the carts and their respective arms. More particularly, the present disclosure is directed to a system and method for registration of the modular arm carts in a surgical robotic system in relation to a surgical table, height adjustment of controls of the surgical console, and a graphical user interface for displaying orientation of an endoscopic camera coupled to one of the robotic arms.

2. Background of Related Art

Surgical robotic systems are currently being used in minimally invasive medical procedures. Some surgical robotic systems include a surgical console controlling a surgical robotic arm and a surgical instrument having an end effector (e.g., forceps or grasping instrument) coupled to and actuated by the robotic arm. In operation, the robotic arm is moved to a position over a patient and then guides the surgical instrument into a small incision via a surgical port or a natural orifice of a patient to position the end effector at a work site within the patient's body.

Prior to utilizing the robotic arm, the robotic arm needs to be oriented. Thus, there is a need for a system to properly orient the robotic arms and a user interface that represents the status of the robotic arms to the operating room staff. Furthermore, there is a need for a surgical console that is adjustable and a graphical user interface for displaying orientation of an endoscopic camera that is coupled to one of the robotic arms.

SUMMARY

According to one embodiment of the present disclosure, a surgical robotic system includes: a surgical table; a plurality of movable carts being oriented toward the surgical table, each of which includes a robotic arm, and an alignment unit configured to determine an orientation of the movable cart and the robotic arm relative to the surgical table; and a computer coupled to each of the plurality of movable carts and configured to calculate a yaw angle for each of the plurality of movable carts.

According to one aspect of the above embodiment, each of the plurality of movable carts is aligned based on an alignment pattern projected by the alignment unit onto a surface. The computer is configured to set a state of each of the plurality of movable carts to an aligned state in response to a confirmation from the alignment unit.

According to another aspect of the above embodiment, each of the plurality of movable carts includes a plurality of wheels and a plurality of brakes. Each of the plurality of movable carts includes a cart controller configured to identify a corresponding movable cart as registered in response to the plurality of brakes being engaged, the corresponding movable cart being aligned, and the robotic arm being docked to an access port. The cart controller is configured to identify the corresponding movable cart as unregistered in response to at least one of the plurality of brakes being disengaged or the robotic arm being undocked from the access port.

According to a further aspect of the above embodiment, the computer is configured to output a user interface having a surgical table representation and a plurality of graphical representations of the plurality of the movable carts. Each of the plurality of graphical representations displaying the yaw angle. The computer is configured to determine whether two adjacent movable carts of the plurality of the movable carts are spaced apart by a predetermined distance based on a difference between yaw angles of the two adjacent movable carts.

According to another embodiment of the present disclosure, a method of aligning a robotic arm with a surgical table is disclosed. The method includes placing a plurality of movable carts around a surgical table, each of the plurality of movable carts includes a robotic arm; projecting an alignment pattern from an alignment unit onto a surface, the alignment unit is operatively coupled to a movable cart of the plurality of movable carts; and prompting a user to manipulate the alignment pattern by adjusting the alignment unit. The method also includes receiving an input indicating that adjustment to the alignment unit is complete; determining an orientation of the alignment pattern relative to a representative coordinate system; determining an orientation of each movable cart of the plurality of movable carts based on the determined orientation of the alignment pattern; and calculating a yaw angle for each of the plurality of movable carts at a computer coupled to the plurality of movable carts.

According to one aspect of the above embodiment, projecting the alignment pattern includes projecting at least two portions of the alignment pattern and are configured to indicate an alignment direction.

According to another aspect of the above embodiment, the method further includes activating an input device disposed on the alignment unit to confirm that adjustment to the alignment unit is complete. The method may further include setting a state of each of the plurality of movable carts to an aligned state in response to a confirmation from the alignment unit.

According to another aspect of the above embodiment, each of the plurality of movable carts includes a plurality of wheels and a plurality of brakes, and the method further includes identifying a movable cart of the plurality of movable carts as registered in response to the plurality of brakes being engaged, the movable cart being aligned, and the robotic arm being docked to an access port. The method may also include identifying the movable cart as unregistered in response to at least one of the plurality of brakes being disengaged or the robotic arm being undocked from the access port.

According to a further aspect of the above embodiment, the method further includes outputting a user interface having a surgical table representation and a plurality of graphical representations of the plurality of the movable carts. The method may also include displaying the yaw angle with each of the plurality of graphical representations. The method may further include determining whether two adjacent movable carts of the plurality of the movable carts are spaced apart by a predetermined distance based on a difference between yaw angles of the two adjacent movable carts.

According to one embodiment of the present disclosure, a surgical robotic system is disclosed. The surgical robotic system includes a surgical table; a control tower including a first display; and a surgical console coupled to the control tower and including a second display. The surgical robotic system also includes a plurality of movable carts coupled to the control tower and configured to be controllable by the surgical console. The plurality of movable carts is oriented toward the surgical table. Each of the movable carts includes a robotic arm having an instrument. The surgical robotic system further includes a user interface displayed on the first display and the second display. The user interface is configured to display orientation of the movable carts and the robotic arms relative to the surgical table.

According to one aspect of the above embodiment, the user interface includes a graphical arm representation for each of the movable carts of the plurality of movable carts. One or more of outline, fill, or color of the graphical arm representation may be used to designate a status of the movable cart. The graphical arm representation may include a yaw angle and a numeric identifier. The graphical arm representation may include an identifier designating a robotic arm having a camera.

According to another aspect of the above embodiment, the user interface displayed on the first display is configured to transition between a setup view and a surgical view. The user interface may include a plurality of views. One view of the plurality of views may be a pre-setup view showing the surgical table without a graphical arm representation.

According to another embodiment of the present disclosure, a method for graphical representation of a surgical robotic system is disclosed. The method includes displaying a first user interface on a first display of a control tower coupled to a plurality of movable carts being oriented toward a surgical table. Each of the movable carts includes a robotic arm. The method also includes displaying a second user interface on a second display of a surgical console coupled to the control tower and the plurality of movable carts. The surgical console is configured to control each of the movable carts and the robotic arms, wherein each of the first user interface and the second user interface is configured to display orientation of the movable carts and the robotic arms relative to the surgical table.

According to one aspect of the above embodiment, the method further includes displaying a graphical arm representation for each of the movable carts of the plurality of movable carts. The method may also include modifying at least one of outline, fill, or color of the graphical arm representation as a status of the movable cart. The method may further include displaying a yaw angle and a numeric identifier as part of the graphical arm representation. The method may also include displaying an identifier designating a robotic arm having a camera as part of the graphical arm representation.

According to another aspect of the above embodiment, the method further includes transitioning between a setup view and a surgical view of the first user interface.

According to one embodiment of the present disclosure, a surgical robotic system is disclosed. The surgical robotic system includes a movable cart including a robotic arm having a camera and a surgical console coupled to the movable cart. The surgical console is configured to move the camera, the surgical console including a display configured to display a video feed from the camera and an orientation indicator displaying orientation of the camera.

According to another embodiment of the present disclosure, a method for displaying orientation of a camera in a surgical robotic system is disclosed. The method includes controlling, through a surgical console, movement of a camera coupled to a robotic arm of a movable cart. The method further includes displaying on a display of the surgical console a video feed from the camera, and displaying on the display of the surgical console an orientation indicator displaying orientation of the camera.

According to one aspect of the above two embodiments, the orientation indicator includes a rotation indicator and a pitch indicator. The rotation indicator includes an arrow rotatable within a bounded region to indicate rotation of the camera about a longitudinal axis defined by the camera. The pitch indicator displays an absolute value of a pitch of the camera. The pitch indicator may also include a line bifurcating a bounded region into a lower portion and an upper portion. The absolute value of the pitch of the camera may be represented by vertical movement of the line within the bounded region.

According to one embodiment of the present disclosure, a surgical robotic system is disclosed. The surgical robotic system includes: a surgical table; a control tower including a first display; and a surgical console coupled to the control tower and including a second display. The surgical robotic system also includes a plurality of movable carts, each of the movable carts includes a robotic arm and is coupled to the control tower and configured to be controllable by the surgical console. The plurality of movable carts is oriented with the robotic arms facing toward the surgical table. The surgical robotic system further includes a user interface displayed on the first display and the second display. The user interface is configured to display orientation of the movable carts and the robotic arms relative to the surgical table.

According to one aspect of the above embodiment, the user interface includes a graphical arm representation for each of the movable carts. At least one of outline, fill, or color of the graphical arm representation may be used to designate a status of a movable cart. The graphical arm representation may include a yaw angle and a numeric identifier. The graphical arm representation may include a camera identifier designating a robotic arm having a camera.

According to another aspect of the above embodiment, the user interface displayed on the first display is configured to transition between a setup view and a surgical view. The user interface may include a plurality of views, wherein one view of the plurality of views is a pre-setup view showing the surgical table without a graphical arm representation.

According to a further aspect of the above embodiment, the surgical system further includes a third display coupled to the surgical console, the third display configured to display orientation of the movable carts and the robotic arms relative to the surgical table. The third display may be configured to display an identification number and an instrument of each of the robotic arms.

According to one embodiment of the present disclosure, a method for graphical representation of a surgical robotic system is disclosed. The method includes displaying a first user interface on a first display of a control tower coupled to a plurality of movable carts, each of the movable carts includes a robotic arm and is oriented with the robotic arms facing toward a surgical table. The method also includes displaying a second user interface on a second display of a surgical console. The surgical console is coupled to the control tower and the plurality of movable carts and is configured to control each of the movable carts and the robotic arms. Each of the first user interface and the second user interface is configured to display orientation of the movable carts and the robotic arms relative to the surgical table.

According to one aspect of the above embodiment, the method further includes displaying a graphical arm representation for each of the movable carts of the plurality of movable carts. The method may also include modifying at least one of outline, fill, or color of the graphical arm representation to reflect a status of a movable cart. The method may also include displaying a yaw angle and a numeric identifier as part of the graphical arm representation.

According to another aspect of the above embodiment, the method further includes displaying a camera identifier designating a robotic arm having a camera as part of the graphical arm representation.

According to a further aspect of the above embodiment, the method also includes transitioning between a setup view and a surgical view of the first user interface. The method may further include displaying a third user interface on a third display of the surgical console. The third user interface may be configured to display orientation of the movable carts and the robotic arms relative to the surgical table. The third user interface may also or alternatively be configured to display an identification number and an instrument of each of the robotic arms.

According to one embodiment of the present disclosure, a surgical robotic system includes a movable cart including a robotic arm having a camera, and a surgical console coupled to the movable cart. The surgical console is configured to move the camera. The surgical console also includes a display configured to display a video feed from the camera and an orientation indicator displaying orientation of the camera.

According to one aspect of the above embodiment, the orientation indicator includes a rotation indicator and a pitch indicator. The rotation indicator includes an arrow rotatable within a bounded region that indicates rotation of the camera about a longitudinal axis defined by the camera. The pitch indicator displays an absolute value of a pitch of the camera. The pitch indicator may also include a line bifurcating a bounded region into a lower portion and an upper portion. The absolute value of the pitch of the camera may be represented by vertical movement of the line within the bounded region.

According to one embodiment of the present disclosure, a method for displaying orientation of a camera in a surgical robotic system is disclosed. The method includes controlling, through a surgical console, movement of a camera coupled to a robotic arm of a movable cart. The method also includes displaying on a display of the surgical console a video feed from the camera and displaying on the display of the surgical console an orientation indicator displaying orientation of the camera.

According to one aspect of the above embodiment, the orientation indicator includes a rotation indicator and a pitch indicator. The rotation indicator includes an arrow rotatable within a bounded region, which is configured to indicate rotation of the camera about a longitudinal axis defined by the camera. The pitch indicator displays an absolute value of a pitch of the camera. The pitch indicator includes a line bifurcating a bounded region into a lower portion and an upper portion. The absolute value of the pitch of the camera may be represented by vertical movement of the line within the bounded region.

According to one embodiment of the present disclosure, a surgical robotic system is disclosed. The surgical robotic system includes a control tower and a plurality of movable carts coupled to the control tower, each of the movable carts including a robotic arm. At least one of the robotic arms has a camera. The surgical robotic system also includes a surgical console coupled to the control tower and configured to control each of the robotic arms and to move the camera. The surgical console also includes a display configured to display a video feed from the camera and an orientation indicator displaying orientation of the camera.

According to one aspect of the above embodiment, the orientation indicator includes a rotation indicator and a pitch indicator. The rotation indicator includes an arrow rotatable within a bounded region to indicate rotation of the camera about a longitudinal axis defined by the camera. The pitch indicator displays an absolute value of a pitch of the camera. The pitch indicator may also include a line bifurcating a bounded region into a lower portion and an upper portion. The absolute value of the pitch of the camera may be represented by vertical movement of the line within the bounded region.

According to one embodiment of the present disclosure, a surgical console for controlling a surgical robotic system is disclosed. The surgical console includes a pair of handle controllers configured to control the surgical robotic system, and an armrest configured to support clinician's arms during operation of the pair of the handle controllers. The armrest is movable along a vertical axis. The surgical console further includes a plurality of foot pedals configured to control the surgical robotic system. The plurality of foot pedals is movable along a horizontal axis. The surgical console also includes a display movable along the vertical axis. The display is configured to display a view of a surgical site. The console also includes a user interface for adjusting at least one of a height of the display along the vertical axis, a height of the armrest along the vertical axis, or a depth of the foot pedals along the horizontal axis.

According to one aspect of the above embodiment, the user interface includes a clinician height adjustment input for entering a clinician's height. The surgical console may further include a computer that is configured to automatically calculate at least one of the height of the display along the vertical axis, the height of the armrest along the vertical axis, or the depth of the foot pedals along the horizontal axis based on the clinician's height.

According to another aspect of the above embodiment, the user interface includes an armrest height adjustment input, a foot pedal depth adjustment input, and a display height adjustment input. Each of the armrest height adjustment input, the foot pedal depth adjustment input, and the display height adjustment input includes an up arrow and a down arrow configured to select a parameter. The up arrow or the down arrow may be disabled upon reaching a respective limit of the parameter.

According to one embodiment of the present disclosure, a method for adjusting a surgical console of a surgical robotic system is disclosed. The method includes inputting through a user interface displayed on a display of a surgical console a clinician's height. The display is movable along a vertical axis. The surgical console further includes an armrest movable along the vertical axis, and a plurality of foot pedals movable along a horizontal axis. The method further includes adjusting at least one of a height of the display along the vertical axis, a height of the armrest along the vertical axis, or a depth of the foot pedals along the horizontal axis based on the clinician's height.

According to one aspect of the above embodiment, the method also includes displaying on the user interface an armrest height adjustment input, a foot pedal depth adjustment input, and a display height adjustment input. The method further includes adjusting at least one of the armrest height adjustment input, the foot pedal depth adjustment input, and the display height adjustment input. The method may also include adjusting at least one of the height of the display along the vertical axis, the height of the armrest along the vertical axis, or the depth of the foot pedals along the horizontal axis based on which input was adjusted.

According to another aspect of the above embodiment, the method further includes displaying an up arrow and a down arrow configured to select a parameter for each of the armrest height adjustment input, the foot pedal depth adjustment input, and the display height adjustment input. The method may also include disabling the up arrow or the down arrow upon reaching a respective limit of the parameter.

BRIEF DESCRIPTION OF THE DRAWINGS

Various embodiments of the present disclosure are described herein with reference to the drawings wherein.

DETAILED DESCRIPTION

Figure 1:
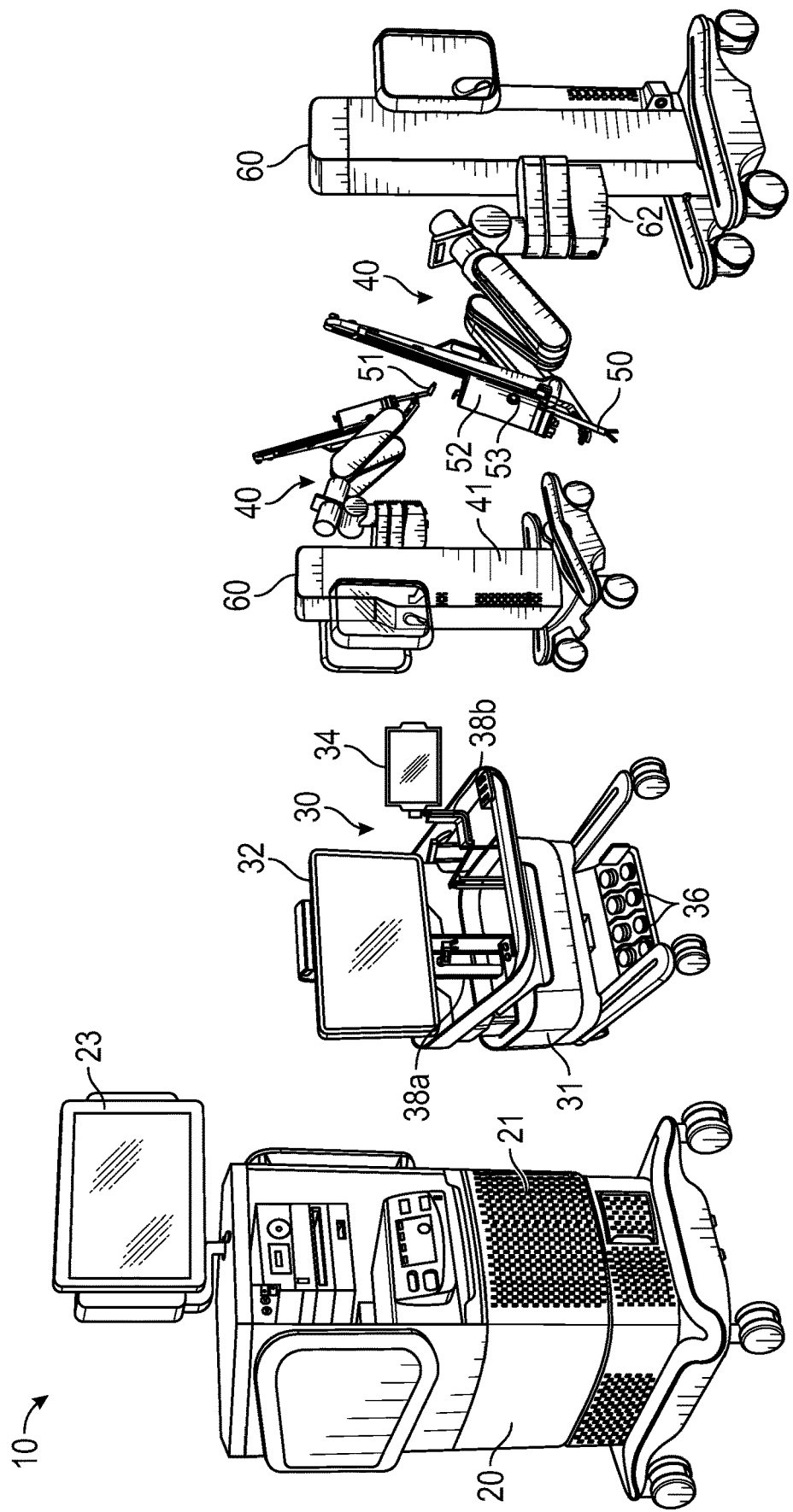
FIG. 1 is a schematic illustration of a surgical robotic system including a control tower, a console, and one or more surgical robotic arms according to the present disclosure.

Embodiments of the presently disclosed surgical robotic system are described in detail with reference to the drawings, in which like reference numerals designate identical or corresponding elements in each of the several views. As used herein the term "distal" refers to the portion of the surgical robotic system and/or the surgical instrument coupled thereto that is closer to the patient, while the term "proximal" refers to the portion that is farther from the patient.

The term "application" may include a computer program designed to perform functions, tasks, or activities for the benefit of a user. Application may refer to, for example, software running locally or remotely, as a standalone program or in a web browser, or other software which would be understood by one skilled in the art to be an application. An application may run on a controller, or on a user device, including, for example, a mobile device, an IOT device, or a server system.

As will be described in detail below, the present disclosure is directed to a surgical robotic system, which includes a surgical console, a control tower, and one or more movable carts having a surgical robotic arm coupled to a setup arm. The surgical console receives user input through one or more interface devices, which are interpreted by the control tower as movement commands for moving the surgical robotic arm. The surgical robotic arm includes a controller, which is configured to process the movement command and to generate a torque command for activating one or more actuators of the robotic arm, which would, in turn, move the robotic arm in response to the movement command.

With reference to FIG. 1, a surgical robotic system 10 includes a control tower 20, which is connected to all of the components of the surgical robotic system 10 including a surgical console 30 and one or more robotic arms 40. Each of the robotic arms 40 includes a surgical instrument 50 removably coupled thereto. Each of the robotic arms 40 is also coupled to a movable cart 60.

The surgical instrument 50 is configured for use during minimally invasive surgical procedures. In embodiments, the surgical instrument 50 may be configured for open surgical procedures. In embodiments, the surgical instrument 50 may be an endoscope, such as an endoscopic camera 51, configured to provide a video feed for the user. In further embodiments, the surgical instrument 50 may be an electrosurgical forceps configured to seal tissue by compression tissue between jaw members and applying electrosurgical current thereto. In yet further embodiments, the surgical instrument 50 may be a surgical stapler including a pair of jaws configured to grasp and clamp tissue whilst deploying a plurality of tissue fasteners, e.g., staples, and cutting stapled tissue.

One of the robotic arms 40 may include a camera 51 configured to capture video of the surgical site. The surgical console 30 includes a first display 32, which displays a video feed of the surgical site provided by camera 51 of the surgical instrument 50 disposed on the robotic arms 40, and a second display 34, which displays a user interface for controlling the surgical robotic system 10. The first and second displays 32 and 34 are touchscreens allowing for displaying various graphical user inputs.

The surgical console 30 also includes a plurality of user interface devices, such as foot pedals 36 and a pair of hand controllers 38a and 38b which are used by a user to remotely control robotic arms 40. The surgical console further includes an armrest 33 used to support clinician's arms while operating the handle controllers 38a and 38b.

The control tower 20 includes a display 23, which may be a touchscreen, and outputs on the graphical user interfaces (GUIs). The control tower 20 also acts as an interface between the surgical console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgical console 30, in such a way that robotic arms 40 and the surgical instrument 50 execute a desired movement sequence in response to input from the foot pedals 36 and the hand controllers 38a and 38b.

Each of the control tower 20, the surgical console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-2003 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
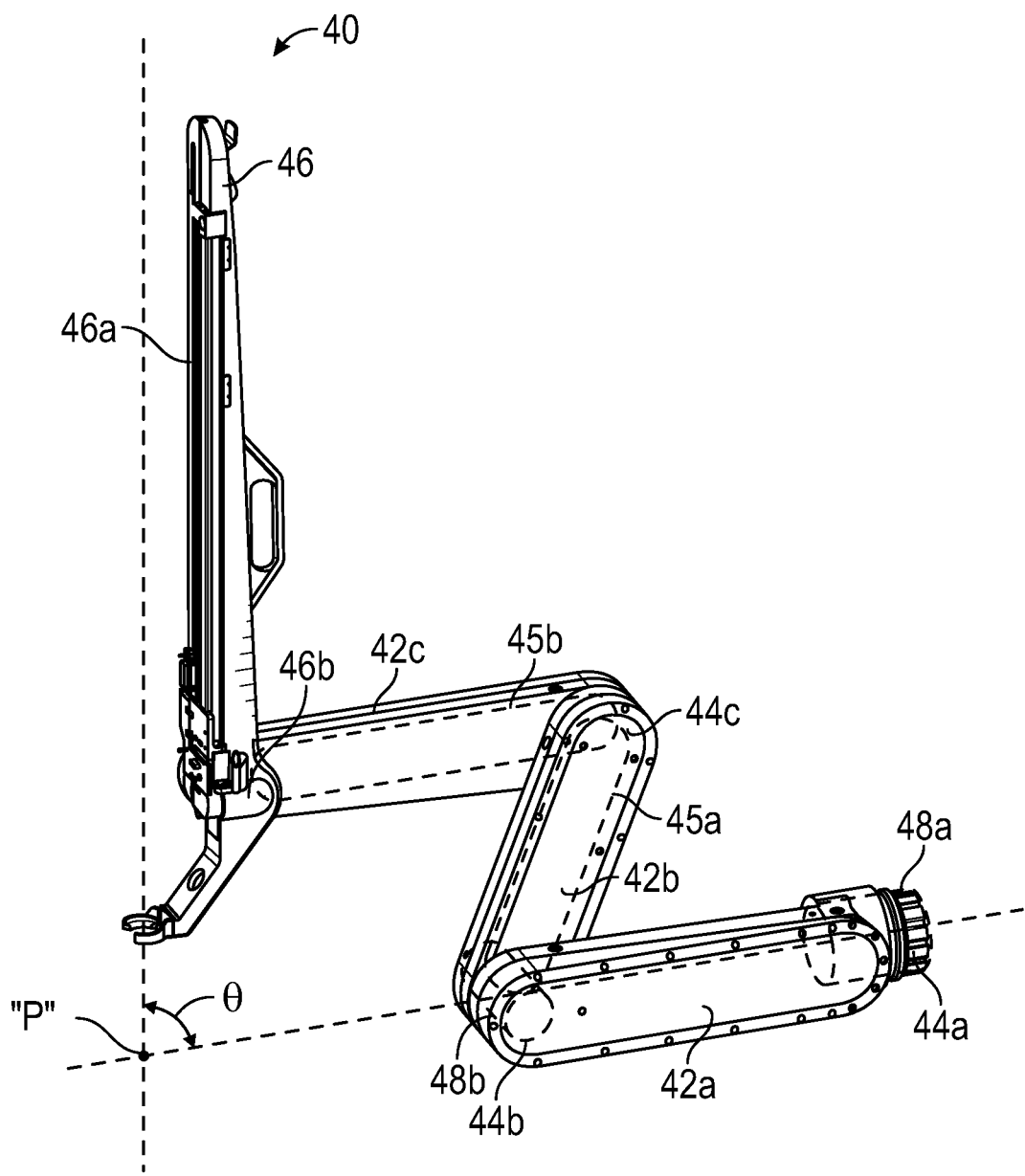
FIG. 2 is a perspective view of a surgical robotic arm of the surgical robotic system of FIG. 1 according to the present disclosure.
Figure 3:
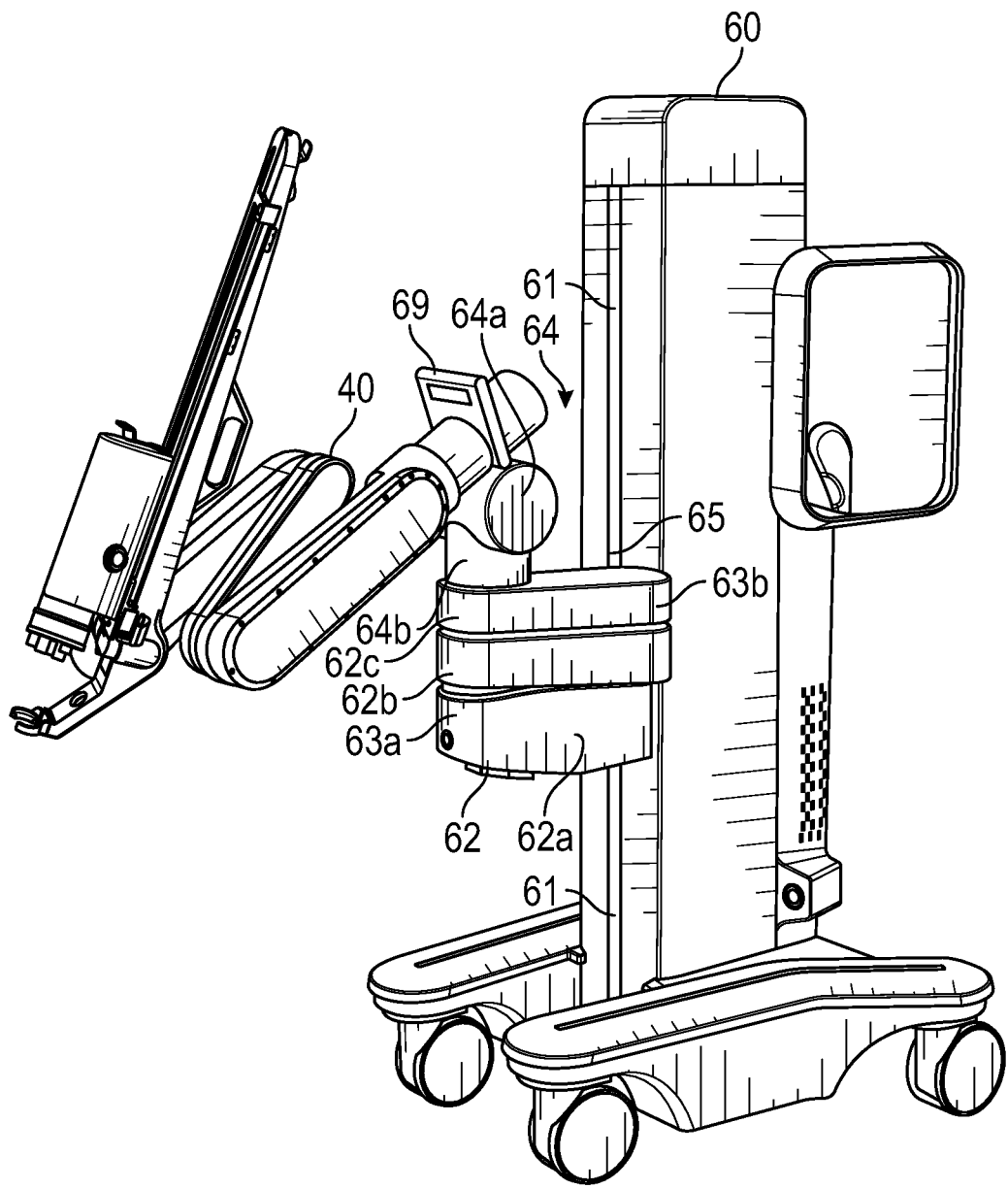
FIG. 3 is a perspective view of a setup arm with the surgical robotic arm of the surgical robotic system of FIG. 1 according to the present disclosure.

With reference to FIG. 2, each of the robotic arms 40 may include a plurality of links 42a, 42b, 42c, which are interconnected at joints 44a, 44b, 44c, respectively. The joint 44a is configured to secure the robotic arm 40 to the movable cart 60 and defines a first longitudinal axis. With reference to FIG. 3, the movable cart 60 includes a lift 61 and a setup arm 62, which provides a base for mounting of the robotic arm 40. The lift 61 allows for vertical movement of the setup arm 62. The movable cart 60 also includes a display 69 for displaying information pertaining to the robotic arm 40.

The setup arm 62 includes a first link 62a, a second link 62b, and a third link 62c, which provide for lateral maneuverability of the robotic arm 40. The links 62a, 62b, 62c are interconnected at joints 63a and 63b, each of which may include an actuator (not shown) for rotating the links 62b and 62b relative to each other and the link 62c. In particular, the links 62a, 62b, 62c are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 62 includes controls 65 for adjusting movement of the links 62a, 62b, 62c as well as the lift 61.

The third link 62c includes a rotatable base 64 having two degrees of freedom. In particular, the rotatable base 64 includes a first actuator 64a and a second actuator 64b. The first actuator 64a is rotatable about a first stationary arm axis which is perpendicular to a plane defined by the third link 62c and the second actuator 64b is rotatable about a second stationary arm axis which is transverse to the first stationary arm axis. The first and second actuators 64a and 64b allow for full three-dimensional orientation of the robotic arm 40.

With reference to FIG. 2, the robotic arm 40 also includes a holder 46 defining a second longitudinal axis and configured to receive an IDU 52 (FIG. 1). The IDU 52 is configured to couple to an actuation mechanism of the surgical instrument 50 and the camera 51 and is configured to move (e.g., rotate) and actuate the instrument 50 and/or the camera 51. IDU 52 transfers actuation forces from its actuators to the surgical instrument 50 to actuate components (e.g., end effectors) of the surgical instrument 50. The holder 46 includes a sliding mechanism 46a, which is configured to move the IDU 52 along the second longitudinal axis defined by the holder 46. The holder 46 also includes a joint 46b, which rotates the holder 46 relative to the link 42c.

The robotic arm 40 also includes a plurality of manual override buttons 53 disposed on the IDU 52 and the setup arm 62, which may be used in a manual mode. The user may press one or the buttons 53 to move the component associated with the button 53.

The joints 44a and 44b include an actuator 48a and 48b configured to drive the joints 44a, 44b, 44c relative to each other through a series of belts 45a and 45b or other mechanical linkages such as a drive rod, a cable, or a lever and the like. In particular, the actuator 48a is configured to rotate the robotic arm 40 about a longitudinal axis defined by the link 42a.

The actuator 48b of the joint 44b is coupled to the joint 44c via the belt 45a, and the joint 44c is in turn coupled to the joint 46c via the belt 45b. Joint 44c may include a transfer case coupling the belts 45a and 45b, such that the actuator 48b is configured to rotate each of the links 42b, 42c and the holder 46 relative to each other. More specifically, links 42b, 42c, and the holder 46 are passively coupled to the actuator 48b which enforces rotation about a pivot point "P" which lies at an intersection of the first axis defined by the link 42a and the second axis defined by the holder 46. Thus, the actuator 48b controls the angle θ between the first and second axes allowing for orientation of the surgical instrument 50. Due to the interlinking of the links 42a, 42b, 42c, and the holder 46 via the belts 45a and 45b, the angles between the links 42a, 42b, 42c, and the holder 46 are also adjusted in order to achieve the desired angle θ. In embodiments, some or all of the joints 44a, 44b, 44c may include an actuator to obviate the need for mechanical linkages.

Figure 4:
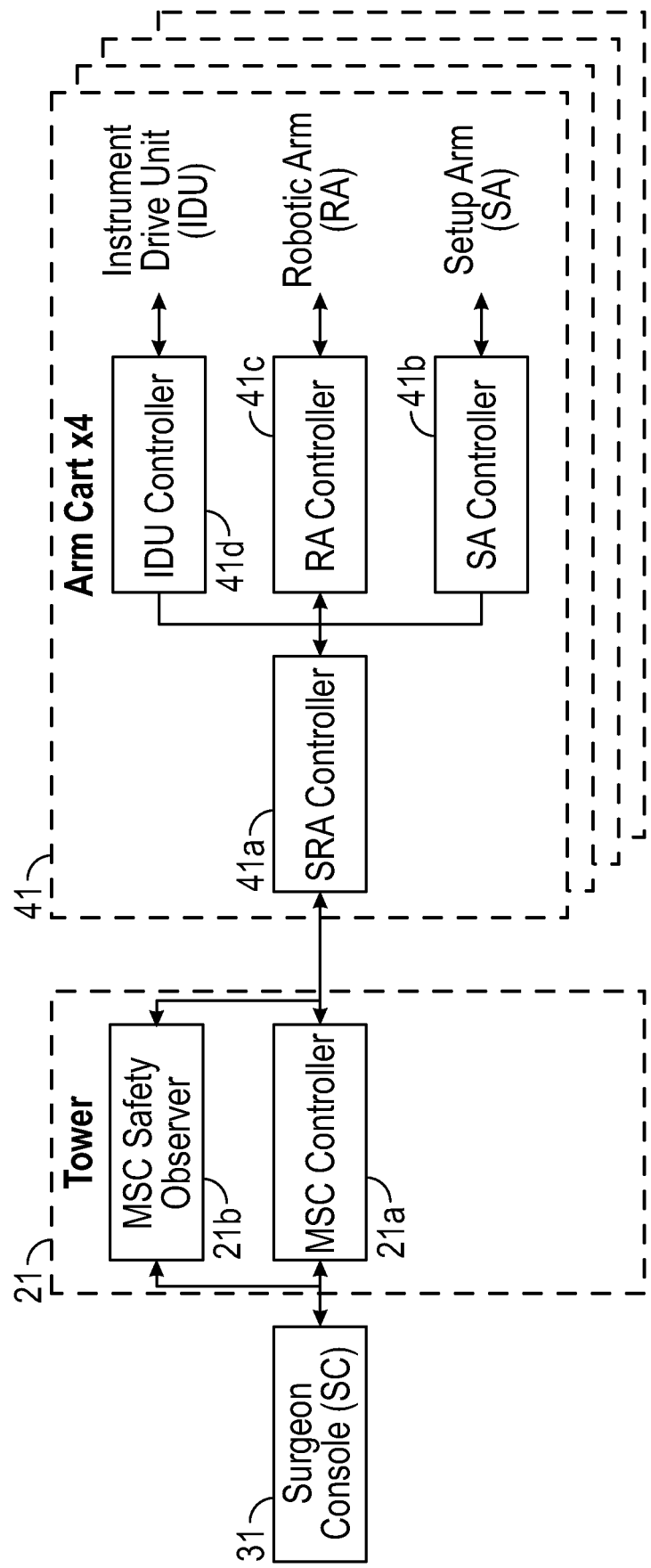
FIG. 4 is a schematic diagram of a computer architecture of the surgical robotic system of FIG. 1 according to the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21a and safety observer 21b. The controller 21a receives data from the computer 31 of the surgical console 30 about the current position and/or orientation of the hand controllers 38a and 38b and the state of the foot pedals 36 and other buttons. The controller 21a processes these input positions to determine desired drive commands for each joint of the robotic arm 40 and/or the IDU 52 and communicates these to the computer 41 of the robotic arm 40. The controller 21a also receives back the actual joint angles and uses this information to determine force feedback commands that are transmitted back to the computer 31 of the surgical console 30 to provide haptic feedback through the hand controllers 38a and 38b. The safety observer 21b performs validity checks on the data going into and out of the controller 21a and notifies a system fault handler if errors in the data transmission are detected to place the computer 21 and/or the surgical robotic system 10 into a safe state.

The computer 41 includes a plurality of controllers, namely, a main cart controller 41a, a setup arm controller 41b, a robotic arm controller 41c, and an instrument drive unit (IDU) controller 41d. The main cart controller 41a receives and processes joint commands from the controller 21a of the computer 21 and communicates them to the setup arm controller 41b, the robotic arm controller 41c, and the IDU controller 41d. The main cart controller 41a also manages instrument exchanges and the overall state of the movable cart 60, the robotic arm 40, and the IDU 52. The main cart controller 41a also communicates actual joint angles back to the controller 21a.

The setup arm controller 41b controls each of joints 63a and 63b, and the rotatable base 64 of the setup arm 62 and calculates desired motor movement commands (e.g., motor torque) for the pitch axis and controls the brakes. The robotic arm controller 41c controls each joint 44a and 44b of the robotic arm 40 and calculates desired motor torques required for gravity compensation, friction compensation, and closed loop position control of the robotic arm 40. The robotic arm controller 41c calculates a movement command based on the calculated torque. The calculated motor commands are then communicated to one or more of the actuators 48a and 48b in the robotic arm 40. The actual joint positions are then transmitted by the actuators 48a and 48b back to the robotic arm controller 41c.

The IDU controller 41d receives desired joint angles for the surgical instrument 50, such as wrist and jaw angles, and computes desired currents for the motors in the IDU 52. The IDU controller 41d calculates actual angles based on the motor positions and transmits the actual angles back to the main cart controller 41a.

The robotic arm 40 is controlled as follows. Initially, a pose of the hand controller controlling the robotic arm 40, e.g., the hand controller 38a, is transformed into a desired pose of the robotic arm 40 through a hand eye transform function executed by the controller 21a. The hand eye function, as well as other functions described herein, is/are embodied in software executable by the controller 21a or any other suitable controller described herein. The pose of one of the hand controller 38a may be embodied as a coordinate position and role-pitch-yaw ("RPY") orientation relative to a coordinate reference frame, which is fixed to the surgical console 30. The desired pose of the instrument 50 is relative to a fixed frame on the robotic arm 40. The pose of the hand controller 38a is then scaled by a scaling function executed by the controller 21a. In embodiments, the coordinate position is scaled down and the orientation is scaled up by the scaling function. In addition, the controller 21a also executes a clutching function, which disengages the hand controller 38a from the robotic arm 40. In particular, the controller 21a stops transmitting movement commands from the hand controller 38a to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the hand controller 38a and is then passed by an inverse kinematics function executed by the controller 21a. The inverse kinematics function calculates angles for the joints 44a, 44b, 44c of the robotic arm 40 that achieve the scaled and adjusted pose input by the hand controller 38a. The calculated angles are then passed to the robotic arm controller 41c, which includes a joint axis controller having a proportional-derivative (PD) controller, the friction estimator module, the gravity compensator module, and a two-sided saturation block, which is configured to limit the commanded torque of the motors of the joints 44a, 44b, 44c.

Figure 5:
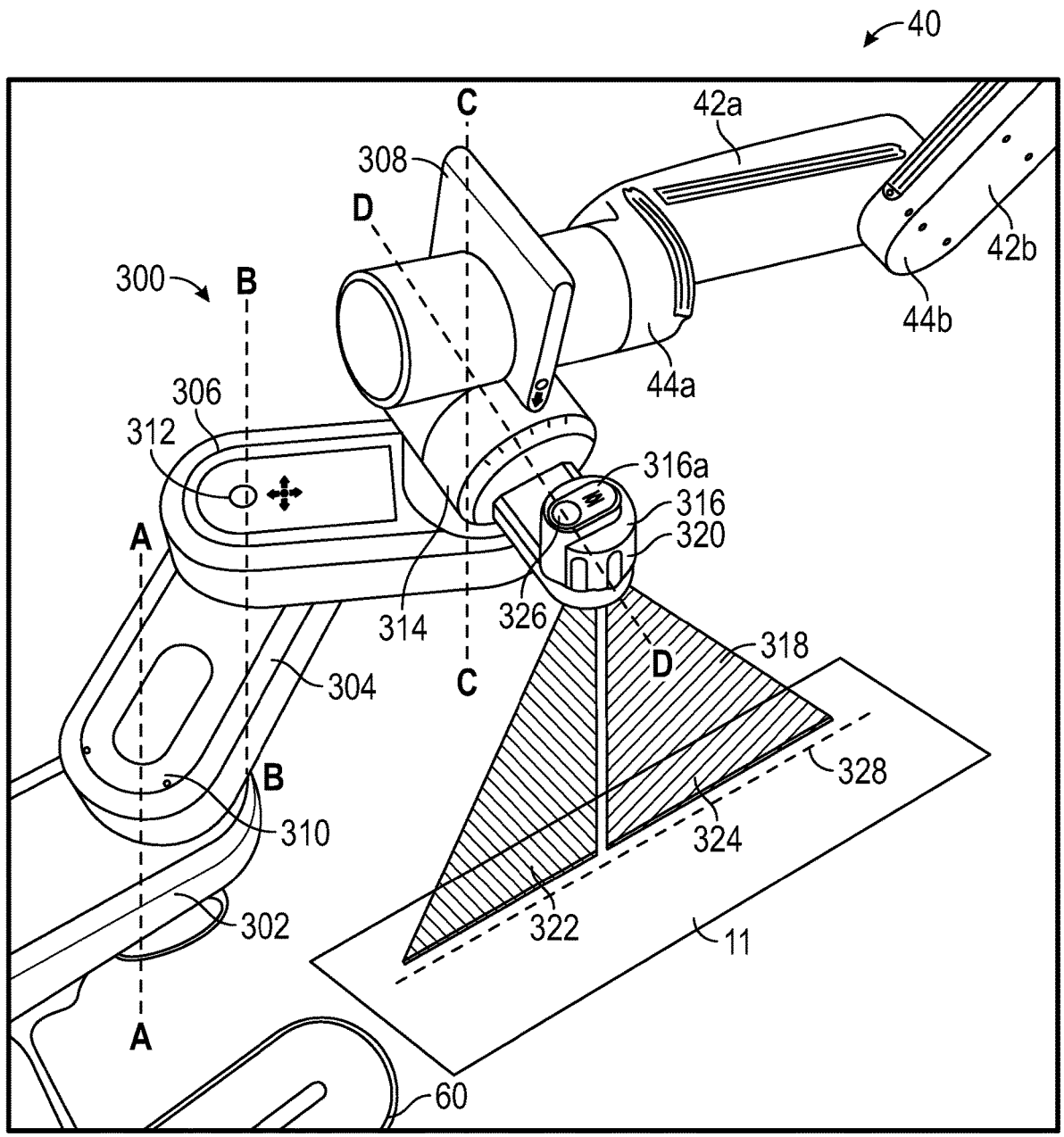
FIG. 5 is a perspective view of the setup arm and the robotic arm of the surgical robotic system of FIG. 1 according to the present disclosure.

With reference to FIG. 5, the robotic arm 40 is coupled to a setup arm 300, which is substantially the same as the setup arm 62. The setup arm 300 is further mounted to the movable cart 60. The setup arm 300 includes a setup arm base 302 that is coupled to the movable cart 60. The setup arm 300 further includes a plurality of movable links that are coupled to each other by actuators (not shown) allowing for movement of the setup arm 300 into various configurations. In particular, setup arm 300 includes a first setup link 304, a second setup link 306, and a coupling assembly 308. The coupling assembly 308 is configured to couple to a robotic arm 40.

The setup arm base 302 is configured to secure the setup arm 300 to a surgical table (not shown) or the movable cart 12. The first setup link 304 is rotatable at a joint 310 360° about an axis "A-A" relative to the setup arm base 302. The second setup link 306 is rotatable at a joint 312 about an axis "B-B" relative to the first setup link 304. The coupling assembly 308 is rotatable at a joint 314 about an axis "C-C" relative to the second setup link 306. The coupling assembly 308 is further rotatable about an axis "D-D" from about 0° to about 90°.

The setup arm 300 includes an alignment unit 316 coupled to the setup arm 300, and in particular to the joint 314. The alignment unit 316 is in operable communication with the control tower 20. In embodiments, the alignment unit 316 may be coupled directly to the coupling assembly 308. The alignment unit 316 is configured to determine the orientation of the setup arm 300 and the robotic arm 40 relative to a representative coordinate system 11, which is a construct generated by the computer 21 and is used to virtually place and orient each of the robotic arms 40 to the clinician viewpoint, e.g., through a camera and/or an endoscope. In particular, the alignment unit 316 is used to create a common reference alignment for the robotic arm 40 and to determine the yaw orientation of the robotic arm 40 relative to the representative coordinate system 11. As used herein the term "yaw" denotes movement of the robotic arm 40 about a vertical axis perpendicular to the ground.

The orientation of each link of the robotic arm 40 and each setup link of the setup arm 300 is used in calculations to make the movement of the robotic arm 40 align with movements of input devices, e.g., manual inputs 18, at the surgical console 30. The alignment unit 316 includes a light unit 412 (see FIG. 6) configured to project an alignment pattern 318 onto a horizontal surface. The alignment pattern 318 may be projected onto any surface, such as a surgical table, a floor, patient, or any other surface. The surface may not be completely horizontal as long as the alignment pattern 318 projected onto the surface is visible and discernable by a clinician or a computing device. Accordingly, any non-vertical surface may be used.

The alignment unit 316 has a rotatable body 320 that allows a user to manually rotate the alignment unit 316 and adjust the angle of the alignment pattern 318 in order to align the alignment pattern 318 with the representative coordinate system 11. In embodiments, the alignment unit 316 may include an indicator 316a, such as a printed label or image on its surface to indicate a forward direction, or a direction relative to the patient. In further embodiments, the alignment pattern 318 may be a line having an indication of a direction. In embodiments, the alignment pattern 318 may include a first portion 324 and a second portion 322. The second portion 322 of the alignment pattern 318 may indicate a forward direction, or a portion of surgical instrument 50 and the robotic arm 40 closest to the patient, and the second portion 322 may indicate a backwards direction, or a portion of surgical instrument 50 and the robotic arm 40 furthest from the patient. The second portion 322 and the first portion 324 may be visually different, such as different colors and/or patterns to allow for easier differentiation. In exemplary embodiments, the second portion 322 may be green and the first portion 324 may be red. In embodiments, the second portion 322 may be blue and the first portion 324 may be yellow to allow for better differentiating by colorblind personnel. In further embodiments, the second portion 322 and the first portion 324 may have different patterns, such as one of the first portion 324 or the second portion 322 may be solid whereas the other may be dashed.

Figure 6:
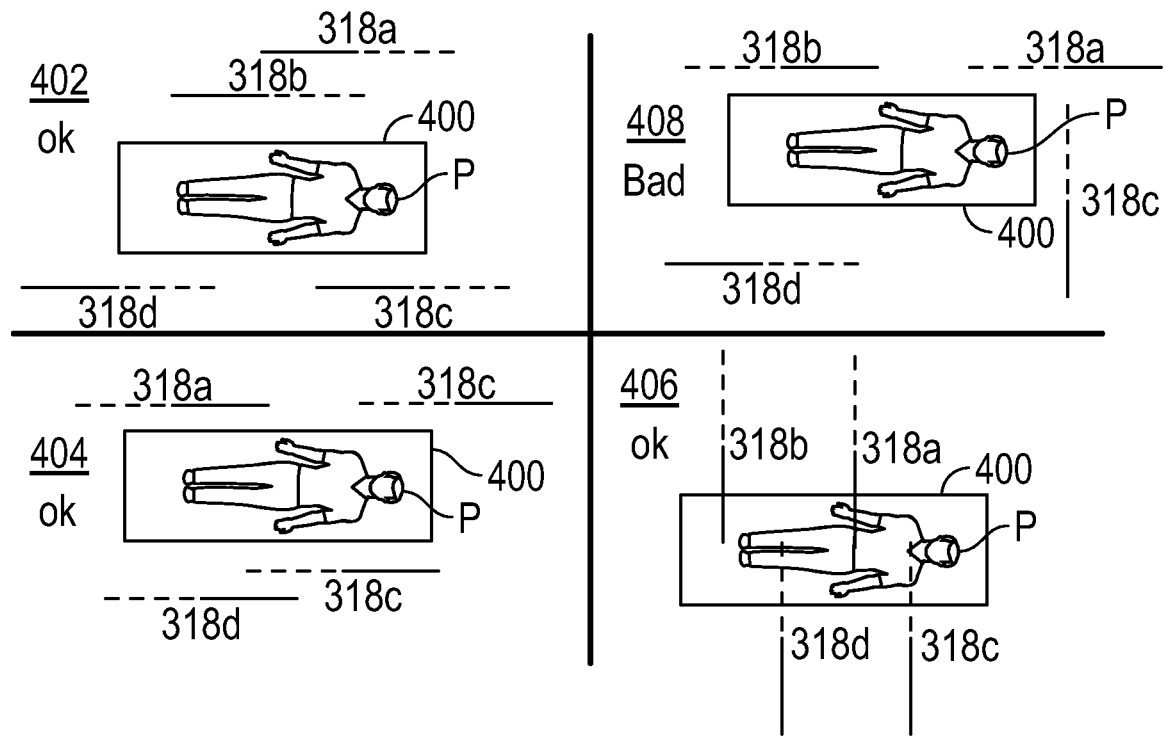
FIG. 6 is a schematic diagram of alignment patterns of the surgical robotic system of FIG. 1 according to the present disclosure.

With reference to FIG. 6, a surgical table 100 is shown with a patient "P" disposed thereon. FIG. 6 also shows a plurality of alignment patterns 318a, 318b, 318c, 318d being oriented relative to the surgical table 100. The surgical table 100 may be used as a reference point for orienting the robotic arms 40 by aligning each of their respective alignment units 316. The reference point may be any object that remains stationary during the period of alignment; such as the surgical table 100, the patient "P", a wall, a marking on the floor, or even any one of the other alignment patterns 318. The alignment patterns 318a, 318b, 318c, 318d projected by the alignment unit 316 of four robotic arms 40. The alignment pattern 318a is projected by the alignment unit 316 attached to the robotic arm 40 holding a camera and/or an endoscope. When properly oriented, the alignment patterns 318b, 318c, 318d are parallel to, and facing the same direction as the alignment pattern 318a projected from the robotic arm 40 holding the camera and/or the endoscope as shown in patterns 402, 404, and 406. Pattern 408 shows misaligned alignment patterns 318a, 318b, 318c, 318d, with the alignment pattern 318c being transverse relative to alignment patterns 318a and 318b and the alignment pattern 318d being oriented in an opposite direction than the alignment patterns 318a and 318b. While pattern 406 shows parallel aligned patterns 318a, 318b, 318c, 318d while the system 10 would correctly coordinate surgeon-controlled motion relative to a camera view, but it would produce an incorrect bed map graphic since all arms would be shown 90 degrees off from their actual yaws.

Figure 7:
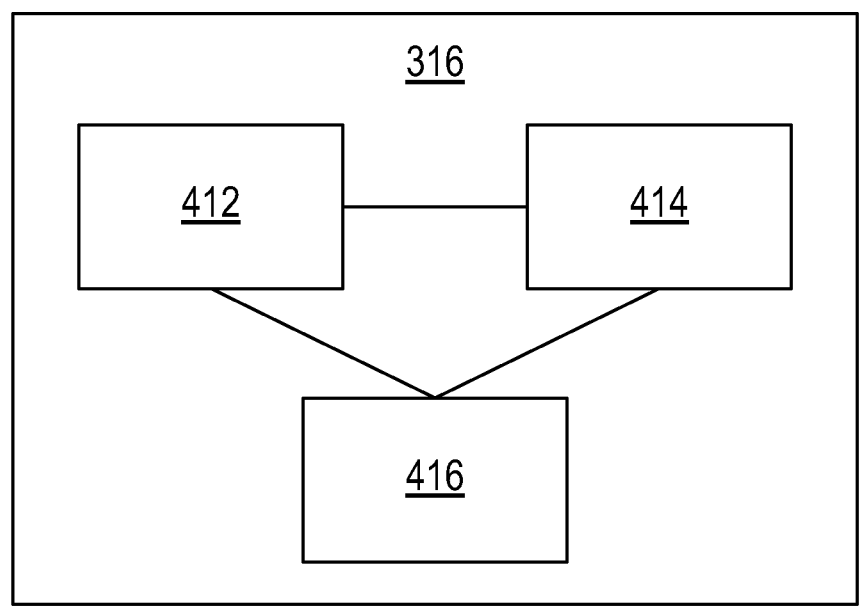
FIG. 7 is a block diagram illustrating the components of the alignment unit.

In embodiments, the alignment unit 316 includes an input device 326, which may be a button or any other user interface device, disposed on the alignment unit 316. The input device 326 is actuatable by a user to indicate to the control tower 20 and/or the surgical console 30 that adjustments to the setup arm 300 and/or the alignment unit 316 are complete. As depicted in FIG. 7, the alignment unit 316 includes a light unit 412, a sensor 414, and a connector 416. The alignment unit 316 may also include a printed circuit board for incorporating various electronic components. The sensor 414 may be any suitable encoder, potentiometer, rotary variable differential transformer, or any other kind of rotary position sensor. In embodiments, the light unit 412 projects a number of different alignment patterns 318, including various shapes, numbers, letters, and/or symbols in one or more colors to help identify an orientation and/or direction of the alignment unit 316. The light unit 412 may include a light source, such as one or more light emitting diodes, which may be configured to emit a laser, and an optional projection pattern or lens, which shapes the emitted light into the alignment pattern 318. The sensor 414 is used to determine the angle of the alignment pattern 318. The sensor 414 may be configured to measure rotation of the alignment unit 316, which is then used to determine the orientation of the robotic arm 40 relative to the representative coordinate system 11. In particular, as the alignment unit 316 is rotated by a user, the sensor 414 determines the angle of the alignment pattern 318 and correlates this angle with a position of the robotic arm 40.

Connector 416 operably couples the alignment unit 316 with the computers 21, 31, and 41 of the control tower 20, the surgical console 30, and the robotic arm 40 and allows for the transfer of data and information to and from the alignment unit 316 and the control tower 20, the surgical console 30, and the robotic arm 40. In embodiments, the connector 416 may be a wired connection (e.g., USB), or connector 416 may include a wireless transmitter/receiver in wireless communication with the control tower 20 and/or surgical console 30, which also may include a wireless transmitter/receiver. The wireless communication may be radio frequency, optical, WiFi®, Bluetooth® (an open wireless protocol for exchanging data over short distances using short length radio waves), etc. Through the connector 416, the control tower 20 and/or surgical console 30 may transfer data and/or real-time data from the alignment unit 316, and more specifically the sensor 414. The sensor 414 senses the orientation of the alignment pattern 318 and sends data regarding the angle of the alignment pattern 318 back to the control tower 20 and/or the surgical console 30. The control tower 20 or the surgical console 30 utilizes this information to correlate movement of the robotic arm 40, relative to the representative coordinate system 11, with movements of input devices, e.g., manual inputs 18, from the surgical console 30.

Figure 8:
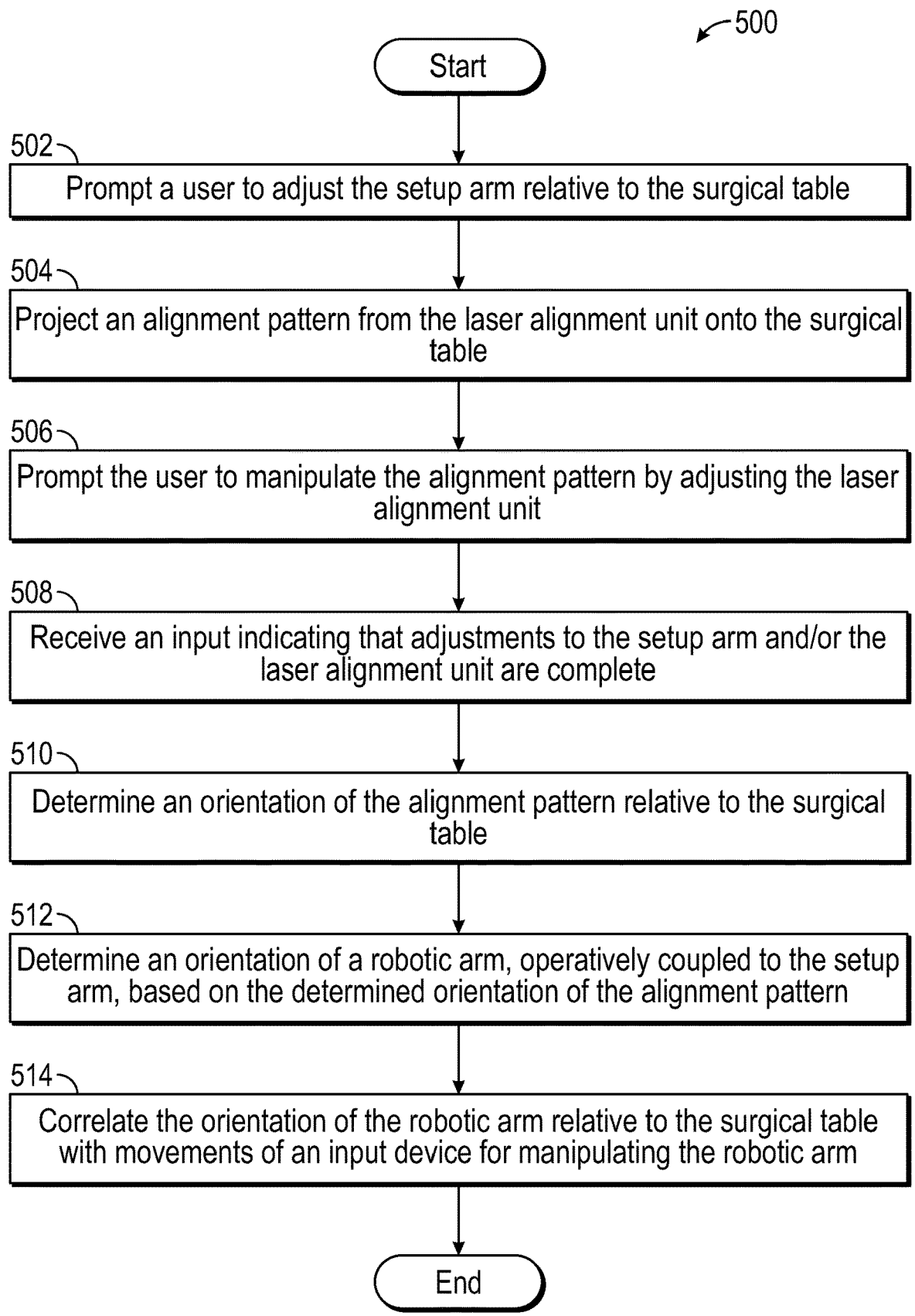
FIG. 8 is a flow chart illustrating a method according to the present disclosure.

FIG. 8 depicts a flow chart 500 of an illustrative method for registering alignment of a robotic arm 40 with the representative coordinate system 11. In practice, when setting up the system at step 502, a user is shown instructions for positioning the movable cart 60, which includes the setup arm 300, robotic arm 40, and surgical instrument 50, adjacent to the representative coordinate system 11. The user then adjusts the setup arm 300, by manipulating the setup links 304, 306, and coupling assembly 308 to align the setup arm 300 with the representative coordinate system 11. In embodiments, the setup links 304, 306 may be manually adjustable by the user. In another embodiment, the setup links 304, 306 may include a plurality of actuators (not shown) configured to actuate the setup links 304, 306. The plurality of motors may be controlled by a control device (not shown) operable by a user. The user may be prompted to re-register the robotic arm 40 with the representative coordinate system 11, according to the disclosed method, if the robotic arm 40 is repositioned, the input device 326 is activated, or if the alignment unit 316 detects a change in yaw of the robotic arm 40. In step 504, once a user adjusts the setup arm 300 relative to the representative coordinate system 11, the alignment unit 316 is configured to project an alignment pattern 318, via the light unit, onto the representative coordinate system 11. The projected alignment pattern 318 may be of high intensity such that the alignment pattern 318 is visible to the user. The alignment unit 316 may be automatically activated once the movable cart 60 is stopped and a cart brake (not shown) is engaged.

In step 506, the user manipulates the alignment pattern 318 by adjusting the alignment unit 316. In particular, the user may rotate the alignment unit 316, which causes the alignment pattern 318 to rotate as well. In embodiments, the alignment pattern 318 may be a straight line. In a further embodiment, the light unit projects two or more colors of light to indicate orientation and/or direction. At step 508, once the user completes adjustments to the alignment unit 316, the user activates input device 326 disposed on the alignment unit 316 to indicate to the control tower 20 and/or the surgical console 30 that adjustments are complete and that the setup arm 300 is properly aligned to the representative coordinate system 11. In embodiments, the movable cart 60 is docked or otherwise connected to the control tower 20. At step 510, the control tower 20 and/or the surgical console 30 determines an orientation of the alignment pattern 318 relative to the representative coordinate system 11. In particular, the alignment unit 316 includes a sensor (not shown) that is used to determine an angle of the projected alignment pattern 318 relative to the position of the alignment unit 316. At step 512, based on the orientation of the alignment pattern 318 relative to the representative coordinate system 11, the control tower 20 and/or the surgical console 30 determines the position and orientation of the setup arm 300 and/or the robotic arm 40 relative to the representative coordinate system 11. At step 514, once the orientation of the robotic arm 40 is determined, the control tower 20 and/or the surgical console 30 correlates the movements and orientation of the robotic arm 40 relative to the representative coordinate system with movements of the manual inputs 18 configured to manipulate the robotic arm.

Figure 9:
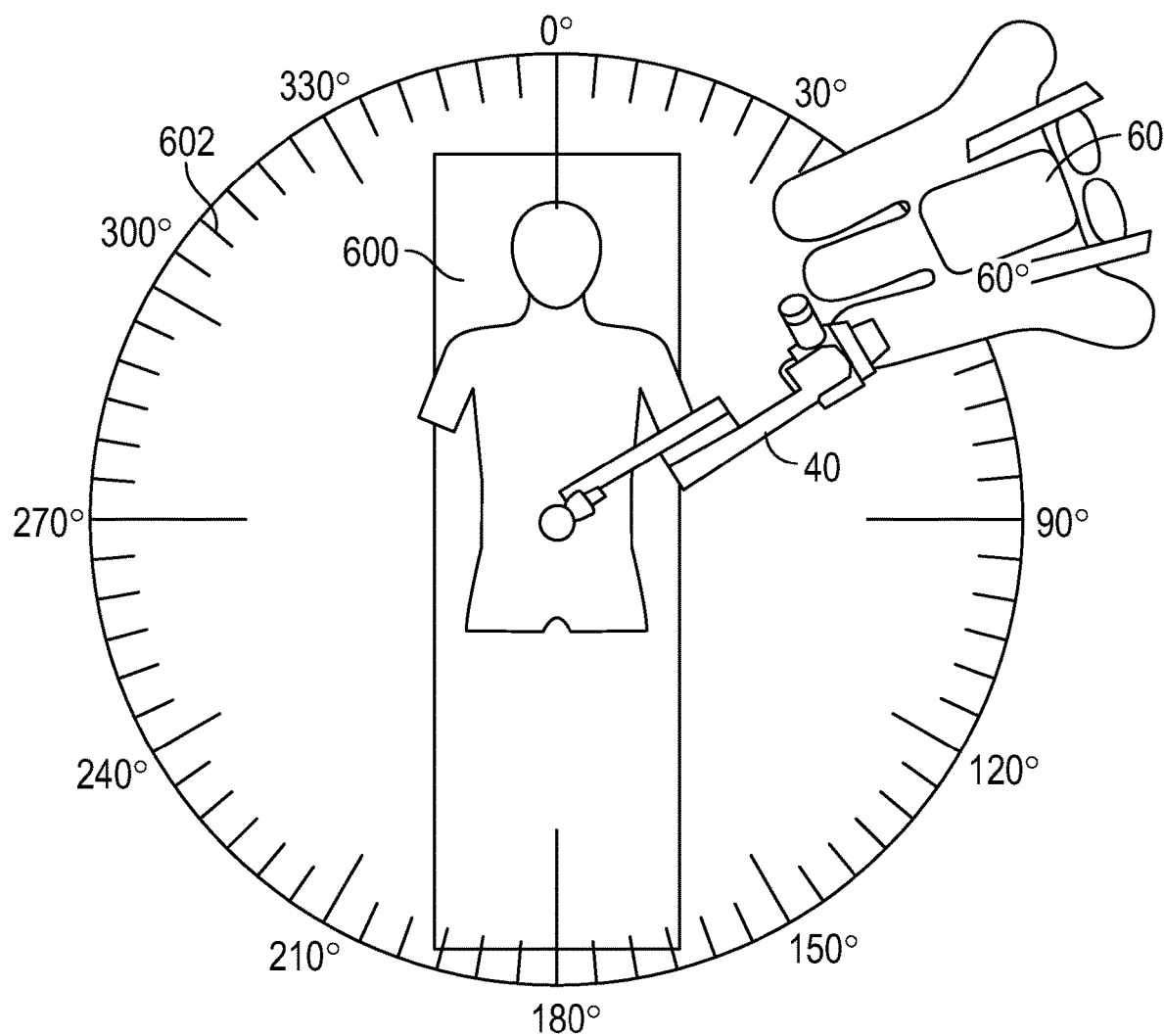
FIG. 9 is a schematic representation of a yaw angle of the robotic arm relative to a surgical table.

The surgical robotic system 10 according to the present disclosure is configured to perform a registration process to correlate (e.g., register) orientation of each of the plurality of movable carts 60 and attached robotic arm 40 relative to a central point in space, such as a surgical table 100 (FIG. 9). During the registration process, the system 10 determines the relative orientation of the robotic arms based on a yaw angle $\phi$ (in a horizontal plane) and the pitch angle $\theta$ (FIG. 2) of the robotic arm 40. As described above, the yaw angle can be controlled by the robotic arm 40 and the setup arm 62 and the pitch angle (e.g., angle can be controlled by the robotic arm 40. Registration of the yaw angle $\phi$ and the pitch angle $\theta$ for each of the robotic arms 40 ensures that handle motion of the hand controllers 38a and 38b from the surgical console 30 correctly maps to natural motion of the surgical instrument 50 on the first display 32 (e.g., moving the hand controller 38a left corresponds to the surgical instrument 50 moving left on the first display 32). The system 10 and in particular the computer 21 of the control tower 20 is configured to execute an algorithm that computes the registration angles (e.g., the yaw angle $\phi$ and the pitch angle $\theta$) for each robotic arm 60 based on the yaw angle $\phi$ as input from the alignment unit 316 as described above with respect to FIGS. 5-8 and the pitch angle $\theta$ as based on the position of the joints 44a, 44b, 44c. After the angles have been registered, the algorithm also determines when the robotic arm 40 and the corresponding movable carts 60 have been registered and handles event logic for controlling the alignment unit 316 and displaying the yaw angle $\phi$ on an arm cart display 69 (FIG. 2). Furthermore, registered and unregistered notifications are sent out to the control tower 20 and the surgical console 30 to indicate the registration state of each movable carts 60. Registration is also confirmed by the operating room staff before performing tele-robotic operation of the surgical robotic system 10.

The main cart controller 41a is configured to perform the registration process and handles setting various registration states for the movable cart 60 and the robotic arm 40. The main cart controller 41a is configured to set the movable cart 60 to a registered state when the following conditions are met: 1) one or more of the brakes 68 are activated to prevent the movement of the movable cart 60, 2) the robotic arm 40 attached to the movable cart 60 is aligned relative to the surgical table 100, and 3) the surgical instrument 50 of the robotic arm 40 is coupled to an access port or trocar (not shown) that is inserted into a patient's abdominal cavity.

Conversely, the main cart controller 41a is configured to set the movable cart 60 to an unregistered state when the following conditions are met: 1) one or more of the brakes 68 are deactivated to allow the movement of the movable cart 60 and 2) the surgical instrument 50 of the robotic arm 40 is decoupled to the port or trocar.

The main cart controller 41a is also configured to set the movable cart 60 to an aligned state when the alignment unit 316 is aligned as described above with respect to FIGS. 5-8 and the input device 326 is activated. In the alignment state, the alignment unit 316 is deactivated and stops emitting the alignment pattern 318.

The controller 21a coordinates communication between operating room team interface (ORTI) and the main cart controller 41a of the movable cart 60. The ORTI is displayed on the display 23 of the control tower 20 as well as the second display 34. The controller 21a is also configured to confirm that each of the robotic arms 40 is registered before teleoperation is enabled for the robotic arm 40 and is further configured to determine when two adjacent robotic arms 40 are too close to each other based on the registered angle. The controller 21a receives the registration status of each robotic arm 40 and publishes data to the main cart controller 41a of each of the movable cart 60 and the ORTI indicating which robotic arms 40 have been user-confirmed, and warnings if the robotic arms 40 are placed too close together.

The controller 21a determines when the movable cart 60 and the robotic arm 40 have been registered, computes the registered yaw angle $\phi$, and handles event logic for controlling the alignment unit 316 and displaying the registered yaw angle on the cart display 69 of the movable cart 60. Furthermore, registered and unregistered notifications are sent out to indicate the registration state of the movable cart 60 and the robotic arm 40. Registration of the movable cart 60 and the robotic arm 40 is confirmed by the operating room staff before teleoperation.

FIG. 9 shows a schematic diagram of the system 10 and in particular, the movable cart 60 and the robotic arm 40, as represented by the controller 21a for storing the yaw angle φ for each of the robotic arm 40 (e.g., a longitudinal axis of the first link 42a of the robotic arm 40) relative to the surgical table 100. Although only one set of a movable cart 60 and robotic arm 40 is shown in FIG. 9, multiple movable carts 60 and corresponding robotic arms 40 may be used. FIG. 9 shows a circular scale 102 having a degree scale from 0° to 360° being oriented with the top of the surgical table 100. In FIG. 9, the robotic arm 40 is shown as having the yaw angle φ of about 60°.

The circular scale 102 and the alignment angles shown thereon follow the right-hand rule (e.g., counter-clockwise), and are defined based on the angle from the alignment pattern 318 to the first link 42a of the robotic arm 40. The angle is zero when the second portion 322 of the alignment pattern 318 is aligned with a longitudinal axis defined by the first link 42a in a forward direction. Conversely, for the system setup and user interface 110 (FIG. 10), the alignment angle is defined clockwise. The angle is zero when the second portion 322 is aligned with the reverse direction of the first link 42a of the robotic arm 40.

The yaw angle is determined by transforming the raw angle of the alignment pattern 318 relative to the surgical table 100 into transformed alignment angle using the following formula (I):

$$\text{alignment angle} = \mod(3*\pi - \text{raw alignment angle}, 2*\pi) \quad (I)$$

In formula (I), the mod function is a modulo operation, which finds the remainder after division of the difference between $3*\pi$ and raw alignment angle by $2*\pi$. The transformed alignment angle is then used to calculate the yaw angle using the formula (II):

$$\text{yaw angle} = \text{transformed laser angle} - \text{sum (current vector} - \text{initial vector)} \quad (II)$$

Figure 10:
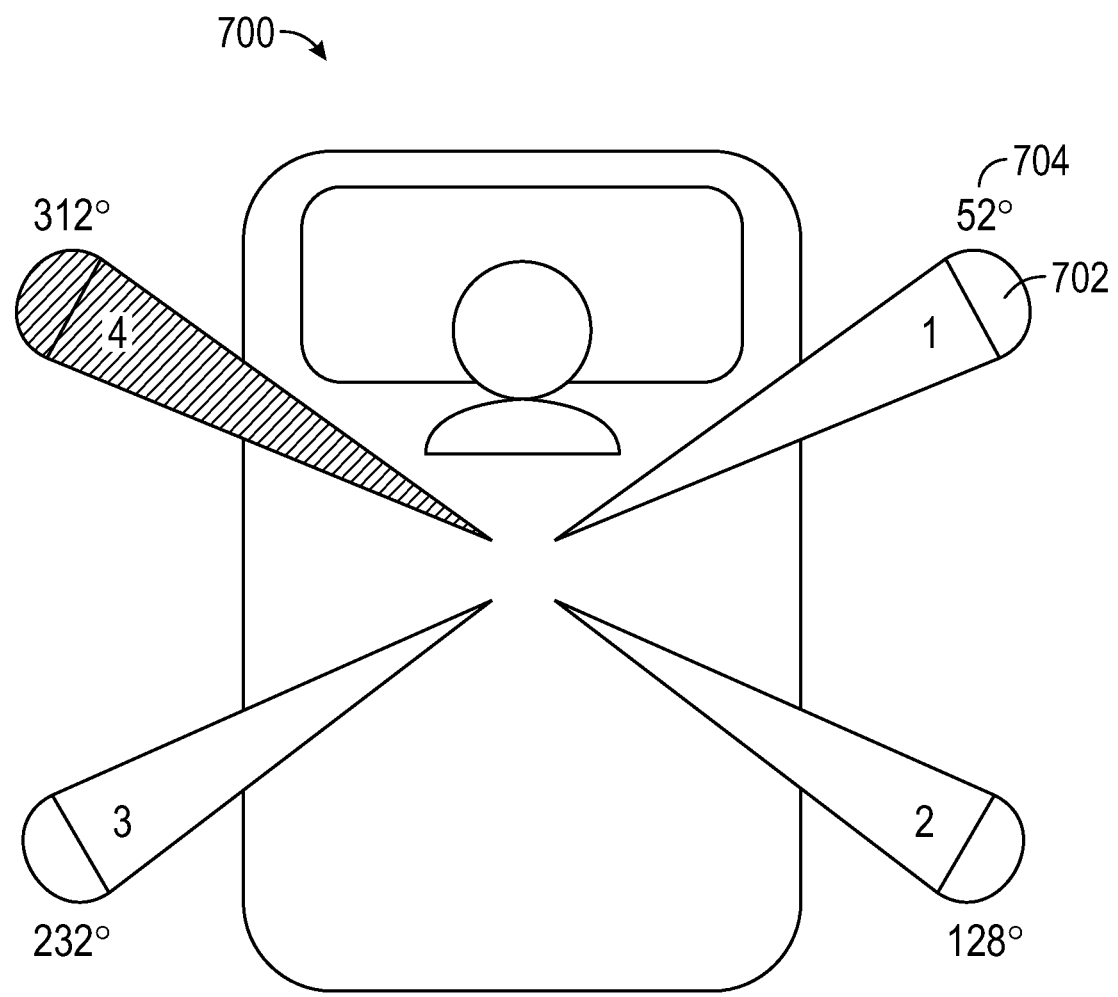
FIG. 10 is a graphical user interface illustrating the yaw angle of the robotic arms relative to the surgical table.

In formula (II), the initial vector is a 3×1 vector of the initial setup arm angles between the links 62a, 62b, 62c of the setup arm 62 prior to alignment and the current vector is a 3×1 vector corresponding to the setup arm 62 being in the post-aligned state. As the robotic arm 40 is moved after its alignment, the current vector is updated, resulting in a new yaw angle being calculated. The yaw angle is displayed for each of the robotic arms 40 on a user interface 110 (e.g., bed map) as shown in FIG. 10. The user interface 110 may be displayed on the first display 32 of the control tower 20 and/or the cart display 69 of the movable cart 60.

When the movable cart 60 along with the robotic arm 40 initially transitions into the aligned state, the yaw angle is equal to the alignment angle. As the setup arm 62 moves during manual plane motion to position the robotic arm 40 relative to the surgical table 100, the rotational joints 63a and 63b rotate about their individual rotation axis that are perpendicular to the floor, so each joint 63a and 63b additively contributes to the rotation of the base joint 44a of the robotic arm 40.

With reference to FIG. 10, the user interface 110 is part of the ORTI and includes a graphical arm representation 112 of each of the robotic arms 40. Each of the graphical arm representations 112 displays an arm identification number 114 and the registered yaw angle 116. In addition, the graphical arm representation 112 is displayed in various colors and/or other indicator to indicate the state of the robotic arms 40.

During setup, the initial, default state for each robotic arm 40 and the movable cart is set to a disabled state, until the brakes 68 have been engaged, at which point the main cart controller 41a transitions to an enabled state and enters an unaligned sub-state. Upon entry into the unaligned sub-state, the laser intensity of the alignment unit 316 is set to high. Once the alignment pattern 318 is aligned with the surgical table 100 and the input device 326 (e.g., laser button) is pressed by the user, the laser intensity is set to off and the point the main cart controller 41a transitions to an aligned state. Upon entry into the aligned state, the raw alignment angle is transformed using formula (I) above. The transformed angle is then used to calculate the yaw angle using formula (II).

When in the aligned state, the main cart controller 41a transitions into an unregistered sub-state, where the flag indicating when to display the yaw angle on the user interface 110 is set to true, upon entry. When the robotic arm 40 is docked, namely, the surgical instrument 50 of the robotic arm 40 is coupled to a port or trocar, the main cart controller 41a transitions to a registered state, the display yaw angle flag is set to false, and the registered flag is set to true. If at any time, in the aligned state, manual mode for the movable cart 60 and the robotic arm 40 is activated, the display yaw angle flag is set to true. Otherwise, if manual mode is not active and the main cart controller 41a is in the registered state, the display yaw angle is set to false. Every time the main cart controller 41a enters the registered state, the registered count value is incremented by one.

In summary, the robotic arm 40 is registered if all of the following conditions are satisfied: the brakes 68 are on, the robotic arm 40 is aligned to the surgical table 100, and the robotic arm 40 is docked, e.g., surgical instrument 50 of the robotic arm 40 is coupled to a port or trocar. Conversely, the robotic arm 40 may become unregistered under any of the following conditions: the robotic arm 40 becomes undocked or the brakes 68 have been released.

The controller 21a of the control tower 20 provides notifications if any of the robotic arms 40 are registered too close to each other (e.g., spaced apart up to a minimum distance), and the controller 21a handles receiving confirmation of registration from the ORTI. The controller 21a determines whether two adjacent robotic arms 40 are close to each other if the difference between the two yaw angles is less than a predetermined threshold. If the robotic arms 40 are too close to each other, the user can either fix the bedside configuration or ignore the notification.

The controller 21a sends a notification to the user specifying which two of the robotic arms 40 are too close together. A notification may be sent for the robotic arms 40 that are registered and are not in manual mode. The controller 21a clears notifications for the robotic arms 40 that are unregistered, in manual plane, or are no longer too close.

Figure 11:
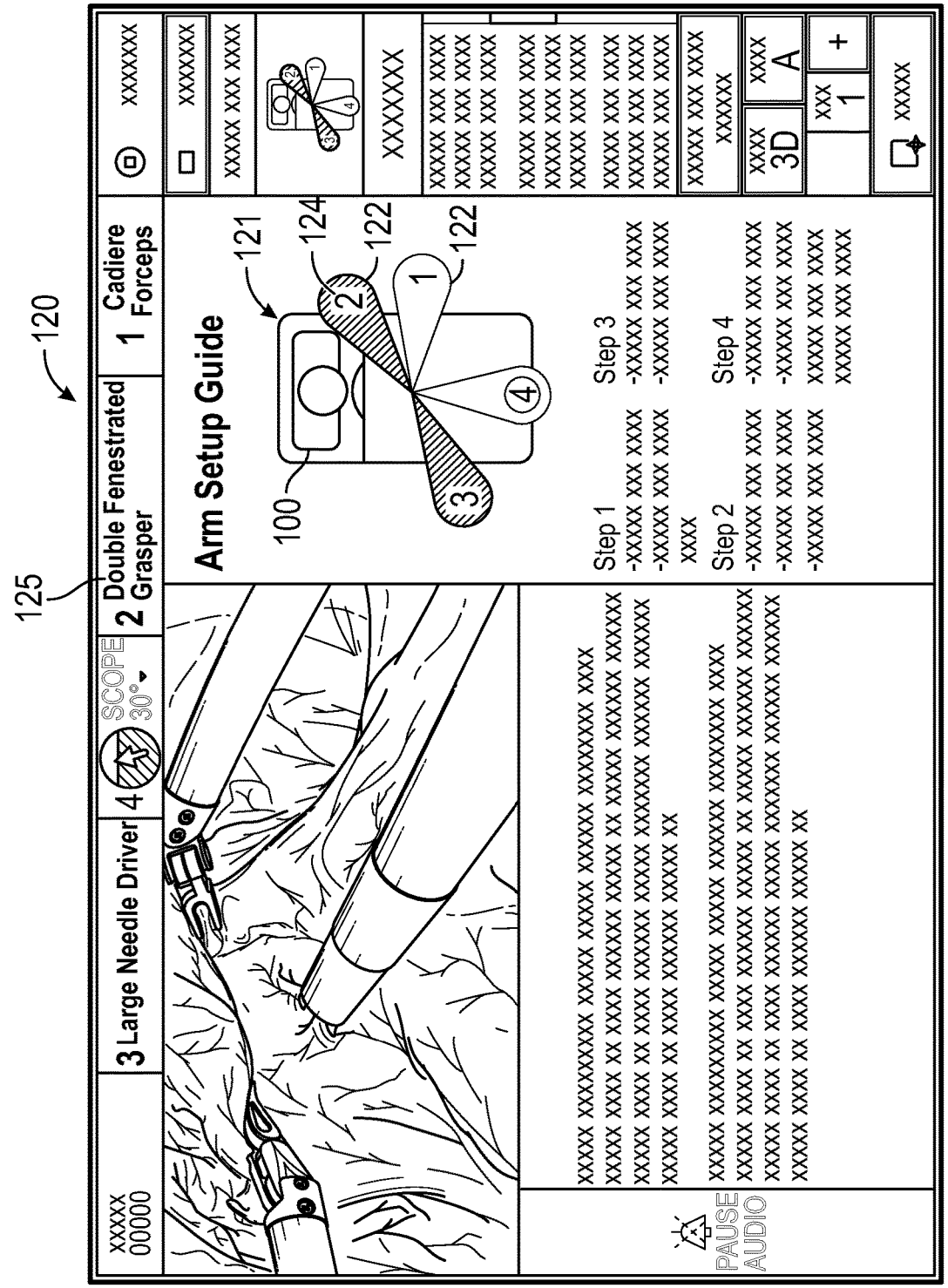
FIG. 11 is a graphical user interface displayed on a display of the control tower according to an embodiment of the present disclosure.
Figure 12:
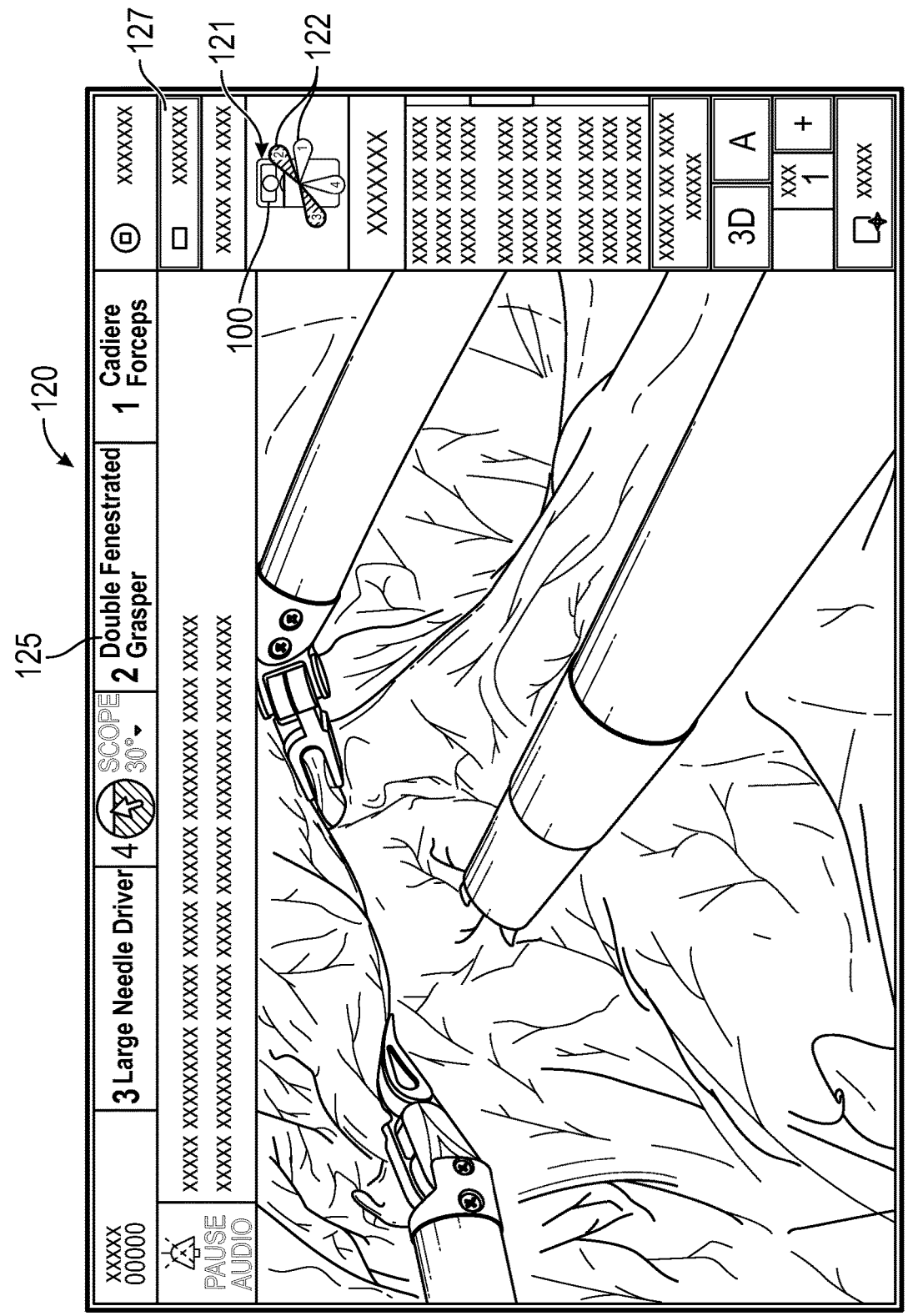
FIG. 12 is a graphical user interface displayed on the display of the control tower according to an embodiment of the present disclosure.

With reference to FIGS. 11 and 12, another embodiment of a user interface 120, which includes similar elements of the user interface 110. The user interface 120 includes a bed map 121 showing a graphical arm representation 122 of each of the robotic arms 40 disposed around the surgical table 100 similar to the interface 110 of FIG. 10.

The bed map 121 allows the users to quickly recognize the relationship of the arms 40 to the patient. The bed map 121 shows the placement of arms 40 relative to the surgical table 100 and patient. Each of the graphical arm representations 122 displays a cart identification number 124, namely 1-4 (FIG. 11), which represents the movable cart 60, the robotic arm 40, and setup arm 62. The user interface 120 displayed on the display 23 of the control tower 20 includes a setup view as shown in FIG. 11 and a surgery view as shown in FIG. 12. The setup view of FIG. 11 shows an enlarged view of the user interface 120 and the surgical view of FIG. 12 is a minimized view of the user interface 120, such that the user interface 120 does not interfere with a surgical view from the camera 51. In addition, the user interface 120 includes a ribbon 125 on top showing the status of each of the robotic arm 40 similar to a user interface 150 of FIG. 13.

Figure 13:
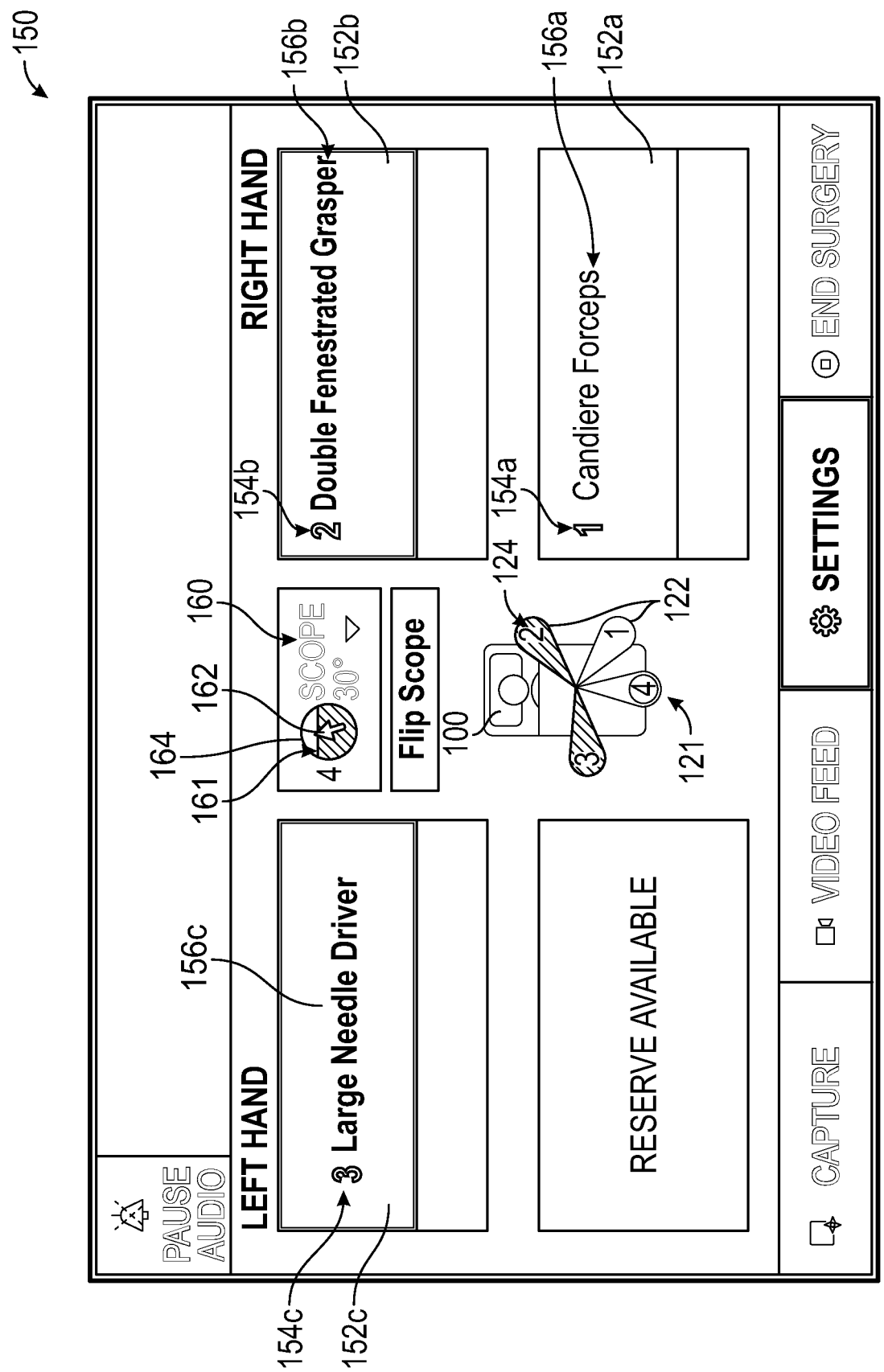
FIG. 13 is a graphical user interface displayed on a second display of the surgical console according to an embodiment of the present disclosure.

There are three instances of the bed map 121 displayed during use of the system 10. The first instance is displayed for the operating team on the display 23 of the control tower 20 during setup (FIG. 11) and during surgery (FIG. 12). During setup, the user may touch an arm setup guide button 127 to switch to the setup view of FIG. 11, in which the bed map 121 is enlarged. The bed map 121 is also displayed as part of a surgeon supplementary user interface 150 on the second display 34 of the surgical console 30 as shown in FIG. 13. The user interface allows the clinician to see the bed map 121 with graphical arm representation 122 for each of the robotic arms 40, similar to the ribbon 125.

Figure 14:
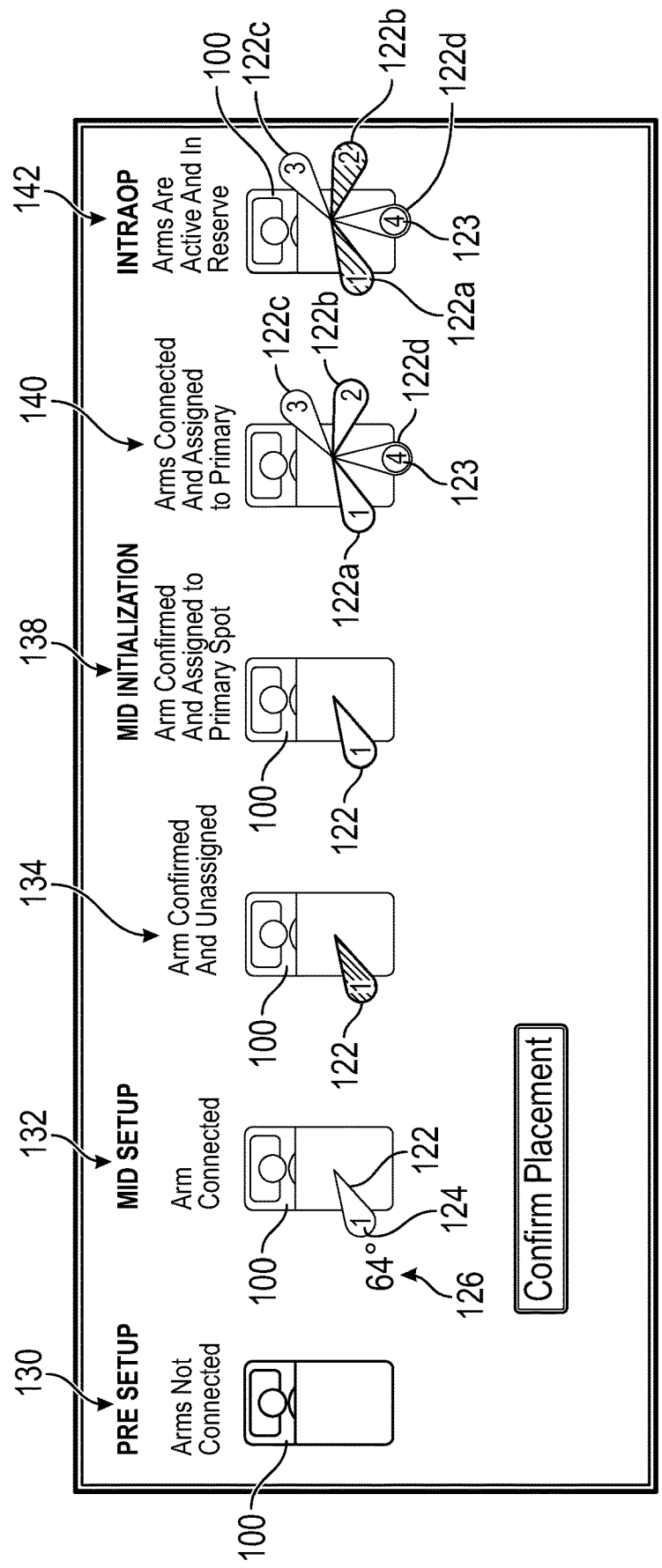
FIG. 14 is a graphical user interface showing a plurality of views during setup of the surgical robotic arms.

With reference to FIG. 14, progression of the registration and designation of each of the robotic arms 40 during their use is shown. The progress may be displayed during the setup view (FIG. 11) on the display 23 of the control tower 20. In particular, FIG. 14 shows progress views of the user interface 120. The first view 130 is a pre-setup view showing the surgical table 100 with no graphical arm representation 122.

Middle setup view includes a second view 132, in which a first robotic arm 40 is connected to the control tower 20. The identification number 124 is assigned to the graphical arm representation 122, which is shown in a dashed outline since the robotic arm 40 is not yet confirmed. In addition, yaw angle 126 of the graphical arm representation 122 is also shown. In a third view 134, the robotic arm 40 is confirmed but is still unassigned. This is illustrated by a transition from a dashed outline to a solid filled graphical arm representation 122.

Middle initialization view includes a fourth view 138, in which the graphical arm representation 122 transitioned from a solid filled representation to a solid line unfilled representation. This illustrates that the robotic arm is confirmed and is assigned to a primary spot. A fifth view 140 shows all of the robotic arms 40 connected, registered and assigned, with each of the graphical arm representations 122a-d being numbered 1-4, respectively. In addition, the fourth graphical arm representation 122d includes a designation 123 for a camera holding robotic arm 40, e.g., using a solid filled circle around the number designation of the arm.

Intra-operational view includes a sixth view 142 with four graphical arm representations 122a-d in which active robotic arms 40 are designated using a first fill or color scheme while robotic arms 40 that are in reserve maintain the same designation as in the fifth view 140. The fill color illustrating active robotic arms 40, namely, the graphical arm representations 122a and 122b, may be a different color combination than the solid filled representation of the third view 134 to avoid confusion. The graphical user interface 120 displayed on each of the displays 23, 32, and 34 may utilize the designations of FIG. 14 to illustrate the status of each of the robotic arms 40.

With reference to FIG. 13, the surgeon supplementary user interface 150, in addition to the bed map 121, also shows a graphical representation 152a-c for each of the three robotic arms 40. Each of the graphical representations 152a-c includes an identification number 154a-c and an instrument type 156a-c since in the depicted scenario only three robotic arms 40 are connected. The user interface 150 also includes an orientation indicator 160. The orientation indicator 160 shows rotation and pitch indication of the camera 51, which shows rotation and pitch indication of the camera 51. The camera 51 may be a stereoscopic camera and provides a real-time video steam of the surgical site. The pitch and rotation of the camera 51 is controlled by one of the hand controller 38a or 38b. Thus, as the hand controller 38a or 38b is rotated about its longitudinal axis, moved vertically and/or laterally that motion is replicated by the camera 51, namely, by the robotic arm 40 and/or the IDU 52. Since the camera 51 is disposed within a confined surgical site orientation of the camera 51 may become confusing to the clinician observing its feed on the display 23 or the first display 32.

Figure 15A:
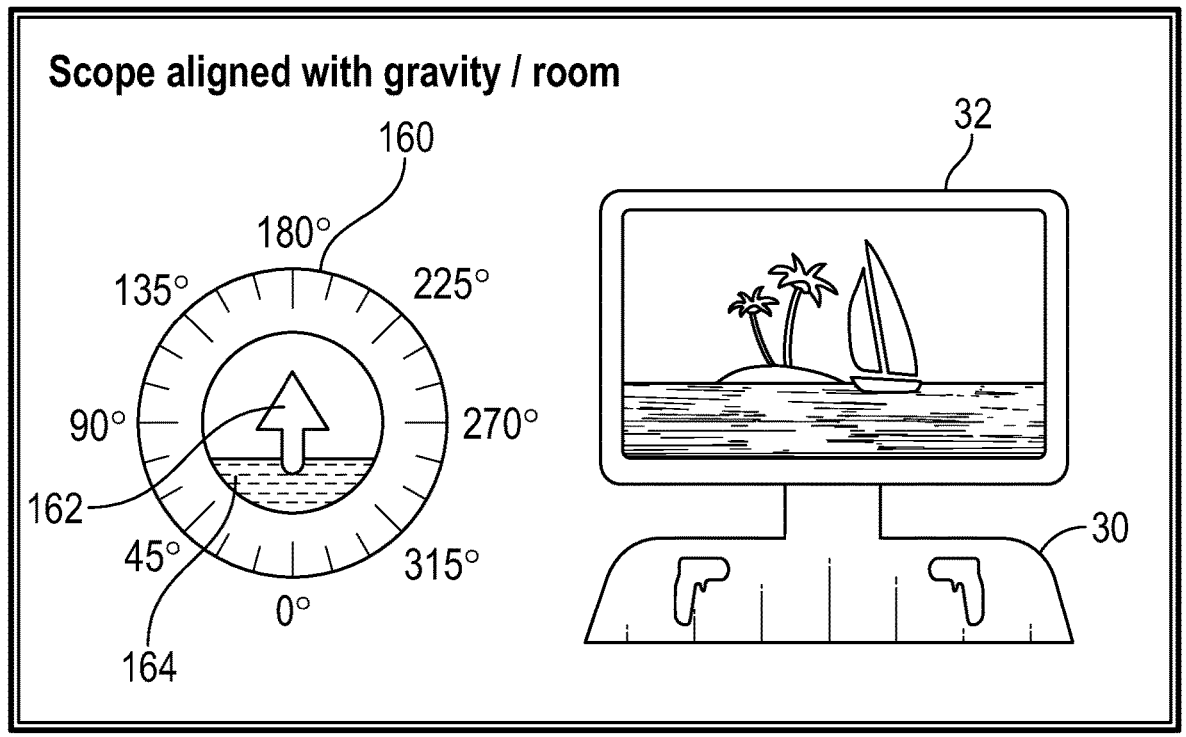
FIGS. 15A-D are graphical user interface representations of a rotation indicator of a camera according to an embodiment of the present disclosure.
Figure 15B:
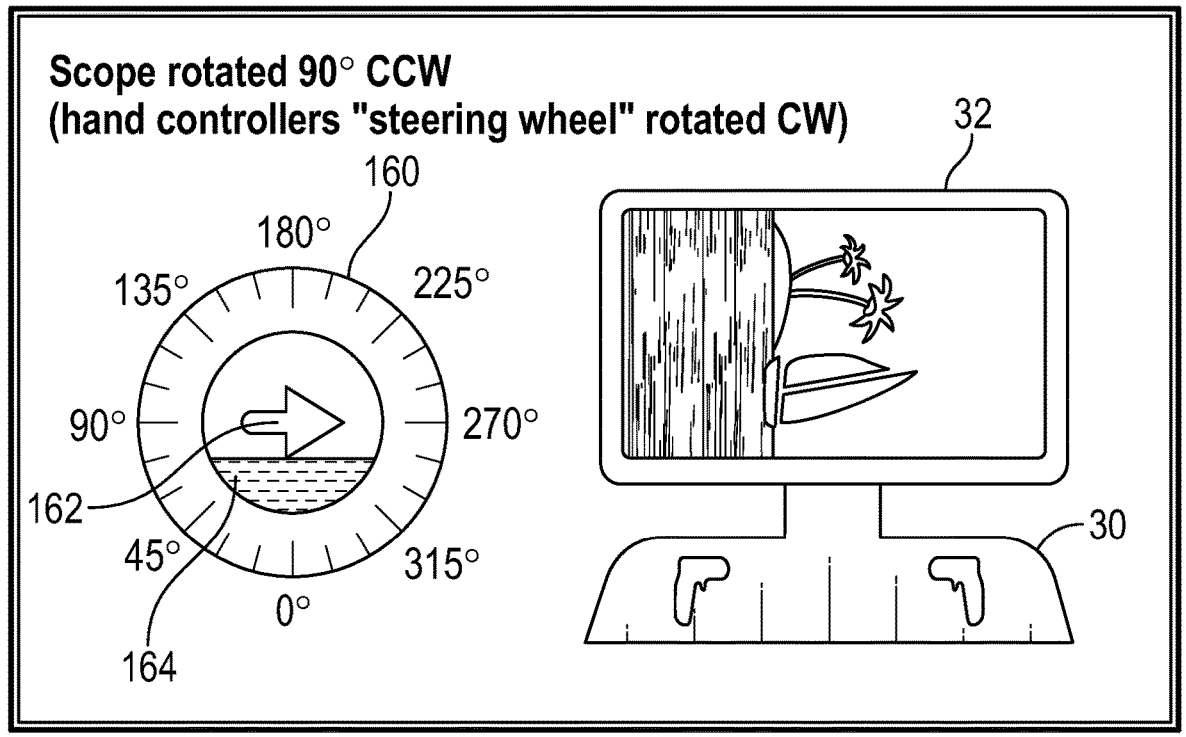
Figure 15C:
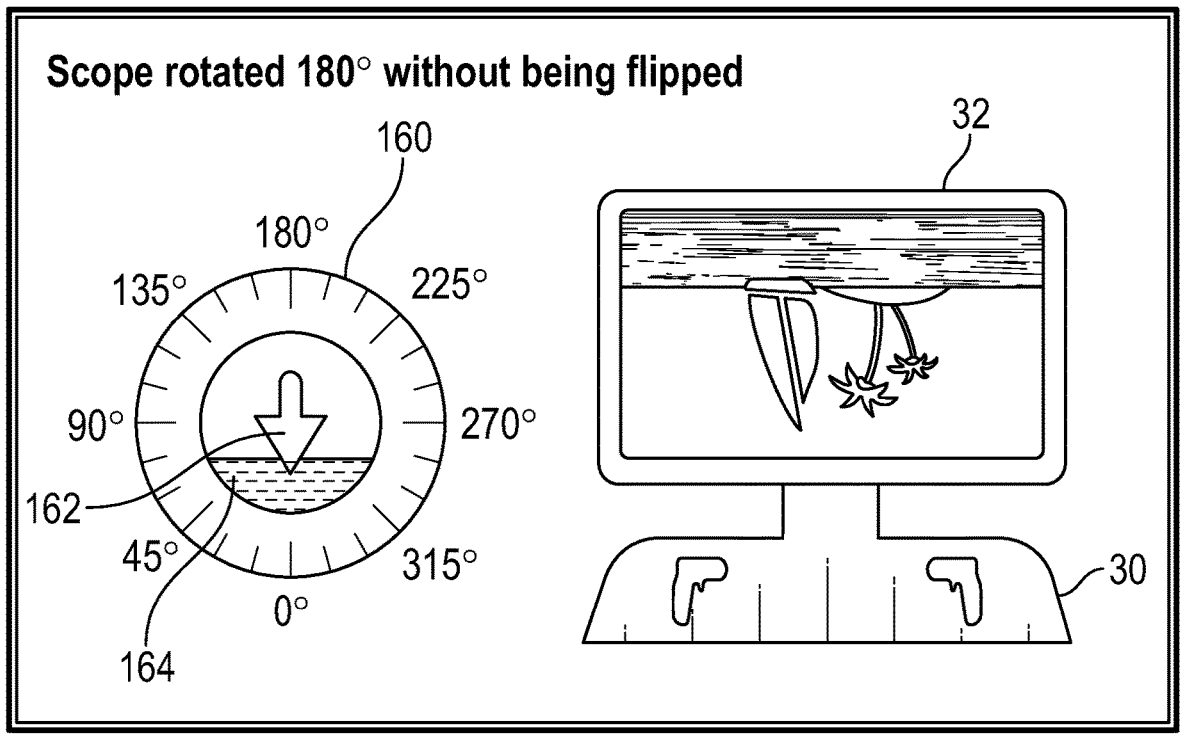
Figure 15D:
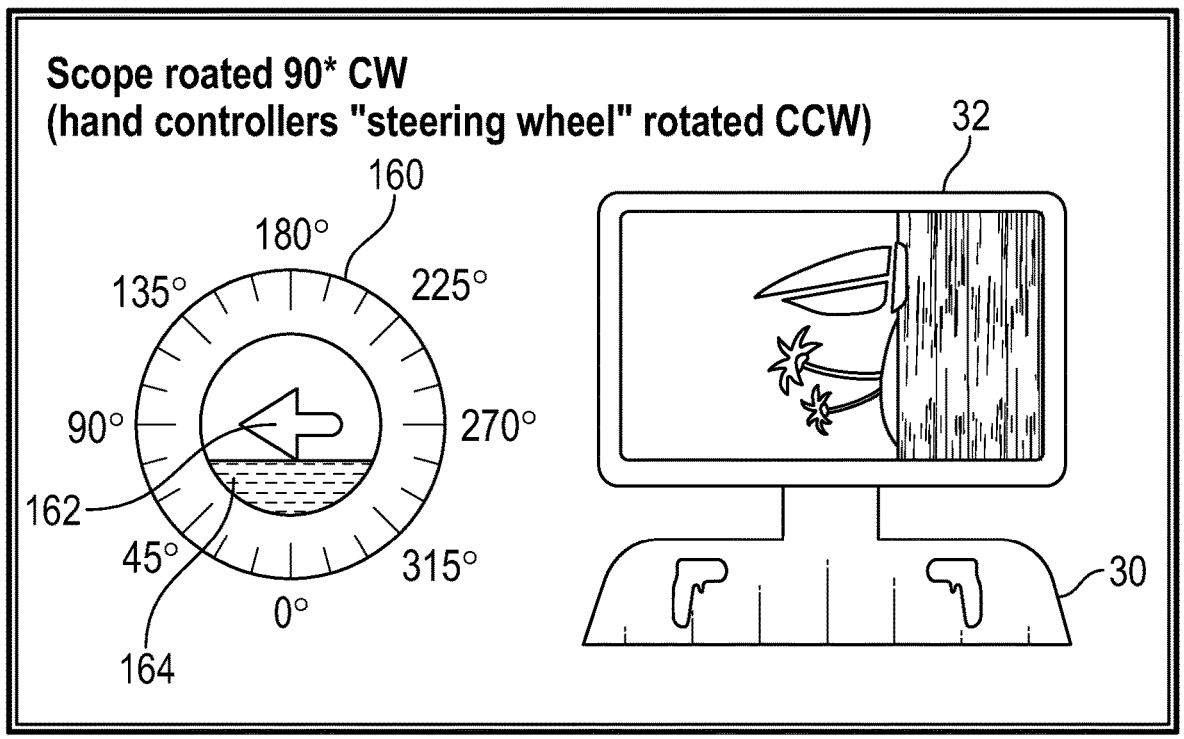

The orientation indicator 160 is a combined a rotation and pitch indicator. A rotation indicator 161 of the orientation indicator 160 includes an arrow 162 disposed within a bounded region 164. As the camera 51 is rotated, the arrow 162 is rotated within the bounded region 164 showing the rotation of the camera 51. With reference to FIGS. 15A-D, as the camera 51 is rotated the view on the first display 32 of the surgical console 30 is rotated as well. The rotation of the camera 51 is also illustrated by the arrow 162 on the orientation indicator 160. In FIG. 15A, the camera 51 is rotated in an upward facing orientation. In FIG. 15B, the camera 51 is rotated 90° clockwise from the position of FIG. 15A. In FIG. 15C, the camera 51 is rotated 90° clockwise from the position of FIG. 15B. In FIG. 15D, the camera 51 is rotated 90° clockwise from the position of FIG. 15C. As shown in FIGS. 15A-D, the direction of the arrow 162 matches the view of the camera 51.

Figure 16A:
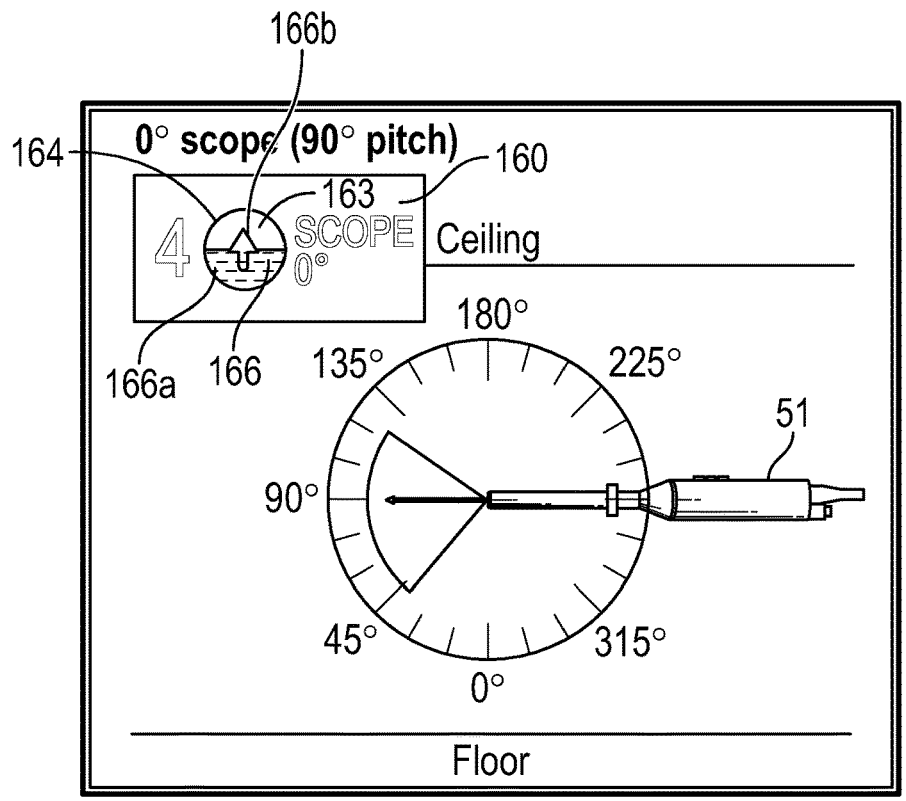
FIGS. 16A-D are graphical user interface representations of a pitch indicator of the camera according to an embodiment of the present disclosure.
Figure 16B:
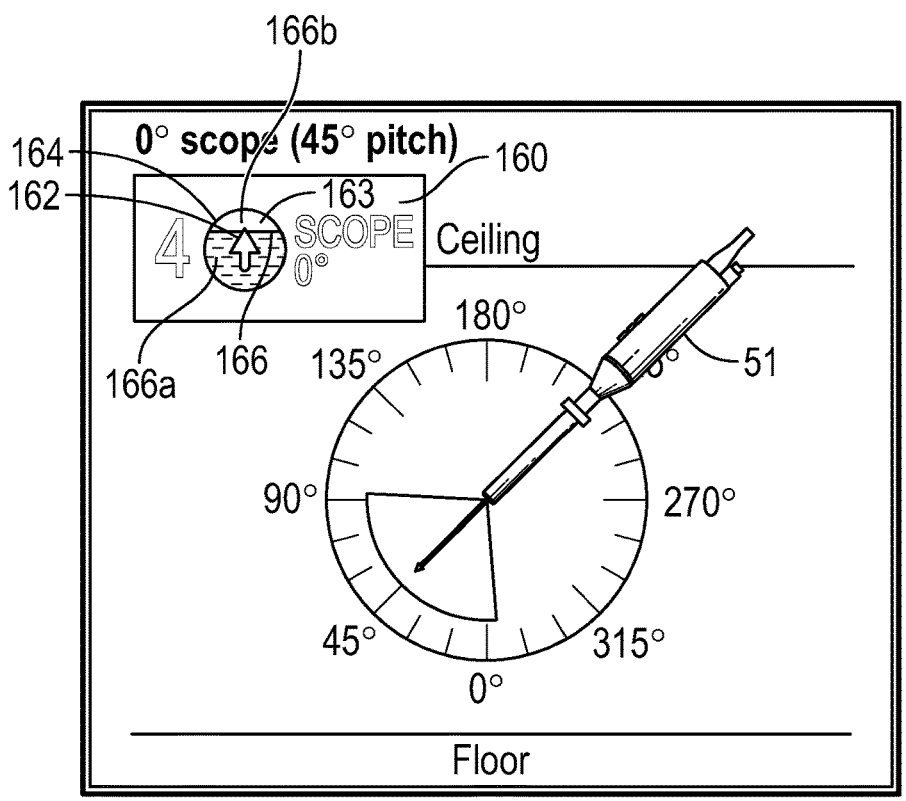
Figure 16C:
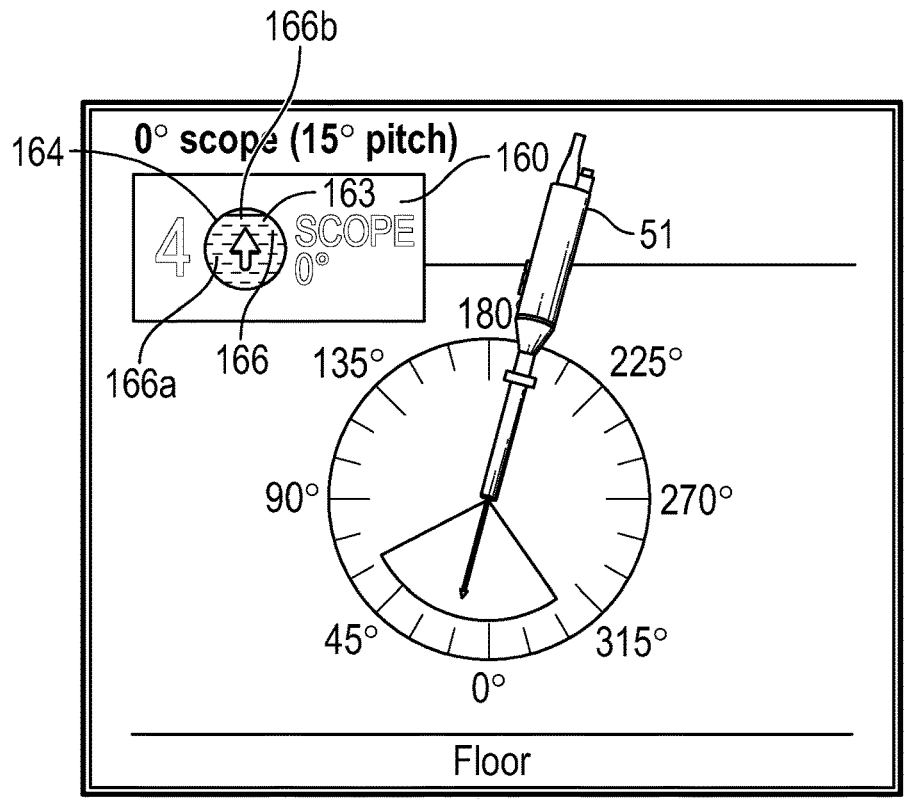
Figure 16D:
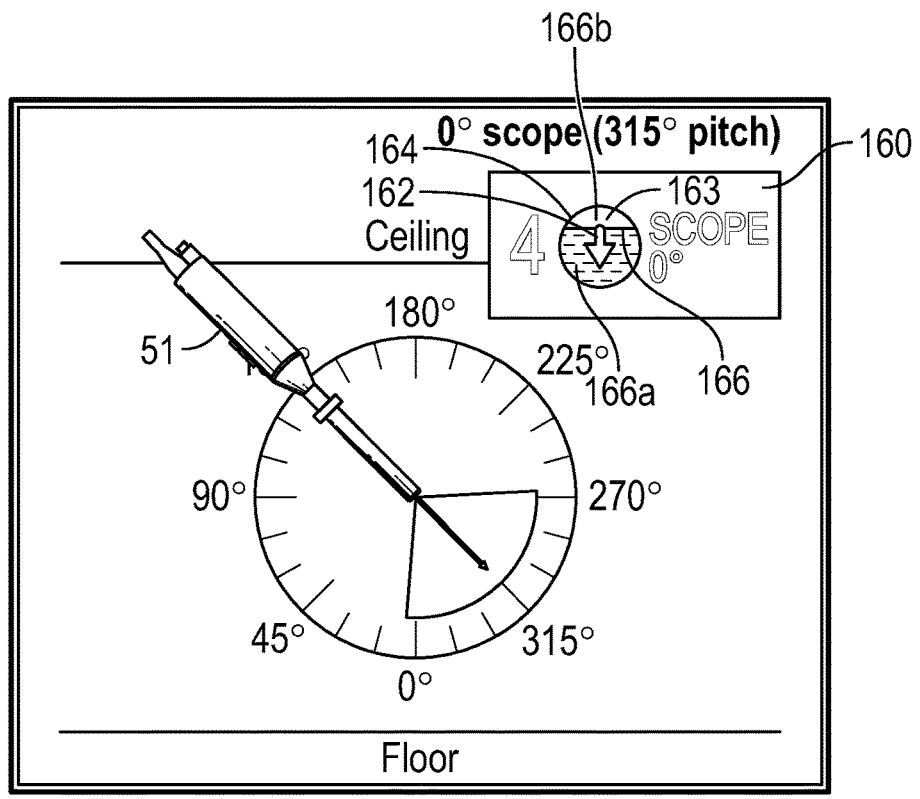

With reference to FIGS. 16A-D, a pitch indicator 163 of the orientation indicator 160 includes a line 166 bifurcating the bounded region 164. The pitch indicator 163 shows an absolute value of the pitch of the camera 51. A lower portion 166a below the line 166 is representative of the floor or ground and an upper portion 166b above the line 166 represents the ceiling or sky. Thus, when the camera 51 is pitched horizontally as shown in FIG. 16A, the portions 166a and 166b are the same. "Absolute value" of pitch denotes that the lower portion 166a is always shown on the bottom. Thus, the amount of the lower portion 166a shown on the indicator is the same when the camera 51 is pitched forward +10° past 0° and when the camera is pitched backward −10° past 0° in the opposite direction (i.e., pitched anywhere on a cone around its vertical axis). As shown in FIGS. 13, 16A-D, and 17A-D the rotation indicator 161 and the pitch indicator 163 both form part of the orientation indicator 160.

Figure 17A:
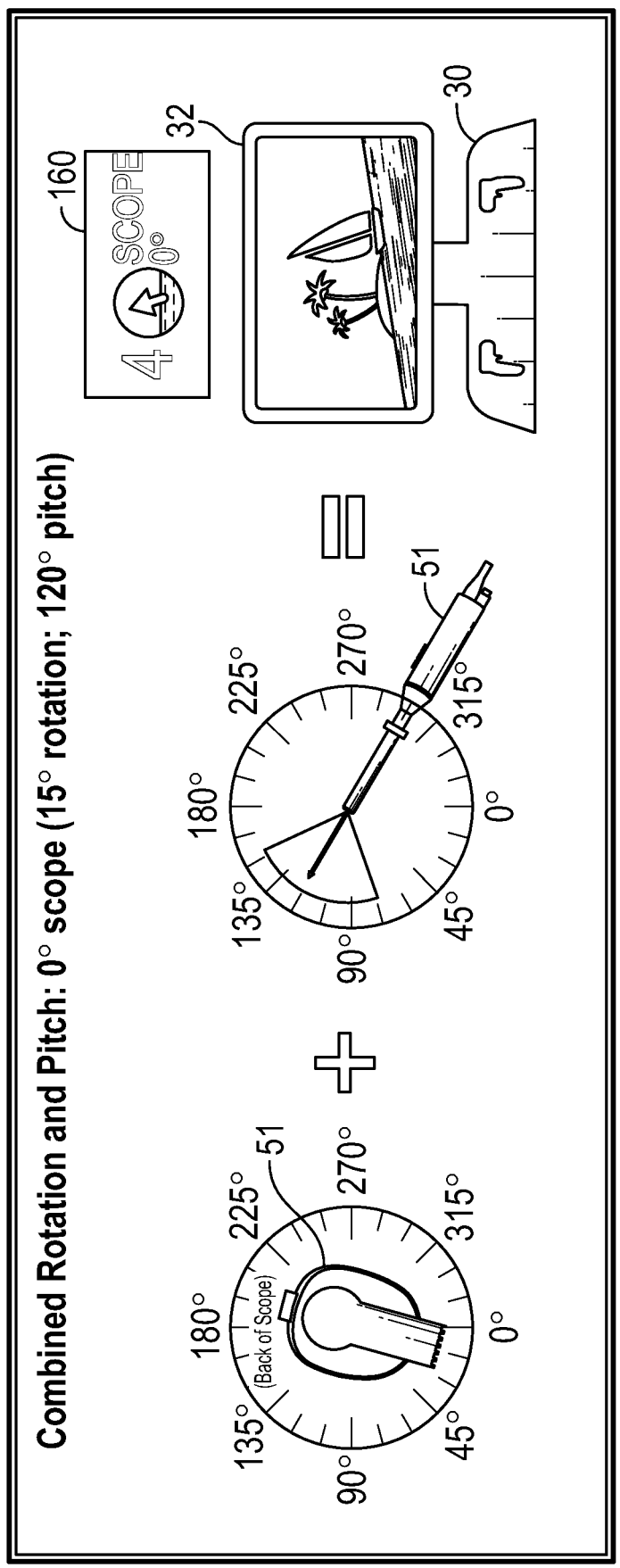
FIGS. 17A and B are graphical user interface representations of a combined orientation indicator having the rotation indicator and the pitch indicator according to an embodiment of the present disclosure.
Figure 17B:
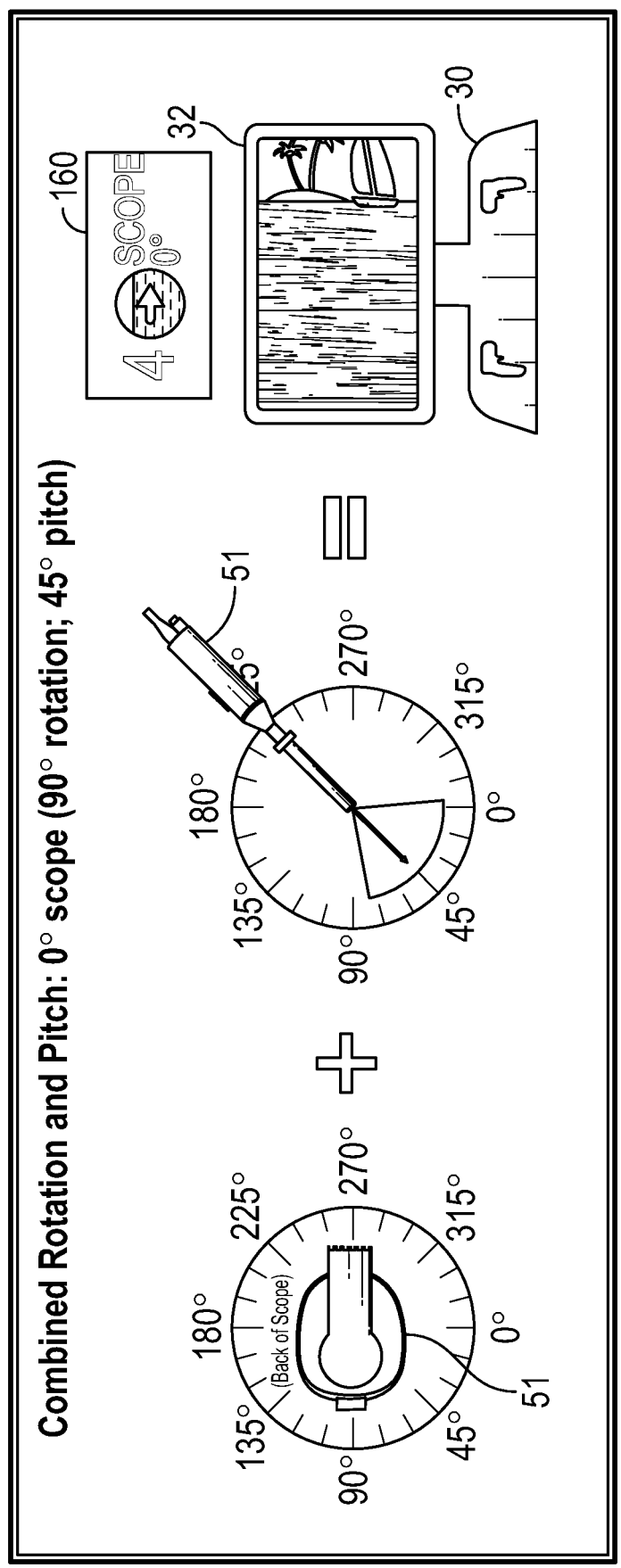

With reference to FIGS. 17A-B, the clinician "drags the workspace," both when rotating the camera 51 and when translating the camera 51. In FIG. 17A, the clinician uses the hand controllers 38a and 38b to "turn the steering wheel counterclockwise" by 15°, and lowers them to raise the view of the camera 51. The camera 51 rotates clockwise (when viewed from behind the camera 51), but the rotation indicator and image on-screen rotate the same direction as the clinician's hands. In FIG. 17B, the clinician turns the hand controllers 38a and 38b clockwise until the camera 51 has rotated 90°, and raises the hand controllers 38a and 38b to lower the endoscope view. The camera 51 itself rotates counterclockwise, but the rotation indicator 161 and image on-screen follow the clinician's hands.

With reference to FIG. 13, the clinician supplementary user interface 150, in addition to the bed map 121, shows additional elements. In particular, the user interface 150 shows a graphical representation 152a-d for each of the four robotic arms 40. Each of the graphical representations 150a-d includes an identification number 154a-c and an instrument type 156a-c since in the depicted scenario only three robotic arms 40 are connected. The user interface 150 also includes an orientation indicator 160. The orientation indicator 160 shows rotation and pitch indication of the camera 51. The camera 51 may be a stereoscopic camera and provides a real-time video steam of the surgical site. The pitch and rotation of the camera 51 is controlled by one of the hand controller 38a or 38b. Thus, as the hand controller 38a or 38b is rotated about its longitudinal axis, moved vertically and/or laterally that motion is replicated by the camera 51, namely, by the robotic arm 40 and/or the IDU 52. Since the camera 51 is disposed within a confined surgical site orientation of the camera 51 may become confusing to the clinician observing its feed on the display 23 or the first display 32.

The orientation indicator 160 is a combined a rotation and pitch indicator. A rotation indicator 161 of the orientation indicator 160 includes an arrow 162 disposed within a bounded region 164. The arrow 162 is rotatable between 0° and 360° such that as the camera 51 is rotated about its longitudinal axis, the arrow 162 is rotated within the bounded region 164 showing the rotation of the camera 51. With reference to FIGS. 15A-D, as the camera 51 is rotated the view on the first display 32 of the surgical console 30 is rotated as well. The rotation of the camera 51 is also illustrated by the arrow 162 on the orientation indicator 160.

With reference to FIGS. 16A-D, a pitch indicator 163 of the orientation indicator 160 includes a line 166 bifurcating the bounded region 164. The pitch indicator 163 shows an absolute value of the pitch of the camera 51. A lower portion 166a below the line 166 is representative of the floor or ground and an upper portion 166b above the line 166 represents the ceiling or sky. Thus, when the camera 51 is pitched horizontally as shown in FIG. 16A, the portions 166a and 166b are the same. "Absolute value" of pitch denotes that the lower portion 166a is always shown on the bottom. Thus, the amount of the lower portion 166a shown on the indicator is the same when the camera 51, such as when the camera 51 is pitched forward e.g., +10° past 0°, and when the camera 51 is pitched backward, e.g., −10° past 0° in the opposite direction (i.e. pitched anywhere on a cone around its vertical axis). Thus, the pitch indicator 163 of FIGS. 16B and D shows the same amount (e.g., absolute value) for the lower and upper portions 166a and 166b, with only the arrow 162 different direction of the camera 51. As the camera 51 is pitched, the line 166 is moved vertically within the bounded region 164. As shown in FIGS. 13, 16A-D, and 17A-D the rotation indicator 161 and the pitch indicator 163 both form part of the orientation indicator 160.

With reference to FIGS. 17A-B, during use, the clinician may drag the workspace shown on the display 32 of the surgical console 30. Dragging the workspace occurs when the camera 51 is both rotated and translated simultaneously. In FIG. 17A, the clinician uses the hand controllers 38a and 38b to turn camera 51 counterclockwise by 15°, and also lowers the hand controllers 38a and 38b to raise the view of the camera 51 since the vertical axis controls are reversed. The camera 51 rotates clockwise (when viewed from behind the camera 51), but the rotation indicator and image on-screen rotate the same direction as the clinician's hands. In FIG. 17B, the clinician turns the hand controllers 38a and 38b clockwise until the camera 51 has rotated 90°, and raises the hand controllers 38a and 38b to lower the endoscope view. The camera 51 itself rotates counterclockwise, but the rotation indicator 161 and image on-screen follow the clinician's hands.

With reference to FIG. 1, certain components of the surgical console 30 may be reconfigured to provide for a tailored ergonomic fit to the clinician. In particular, the height of the first display 32, which provides a 3D view of the surgical site from the camera 51 to the clinician, is adjustable. In addition, the height of the armrest 33 is also adjustable. Furthermore, the depth of the foot pedals 36 is adjustable. Modifying any combination of the ergonomic parameters, namely, the height of the first display 32, the height of the armrest 33, and the depth of the foot pedals 36 allows for achieving a comfortable position for the clinician. Each of the first display 32, the armrest 33, and the foot pedals 36 may be disposed on one or more tracks or other mechanisms that provide for movement of the first display 32, the armrest 33, and the foot pedals 36 along their respective movement axes. In embodiments, the first display 32 and the armrest 33 may be movable along a vertical axis and the foot pedals 36 may be movable along a horizontal axis. In further embodiments, the first display 32, the armrest 33, and the foot pedals 36 may be movable along multiple axis and/or rotatable about a pivot point using ball joints, arms, and other suitable mechanisms.

Figure 18:
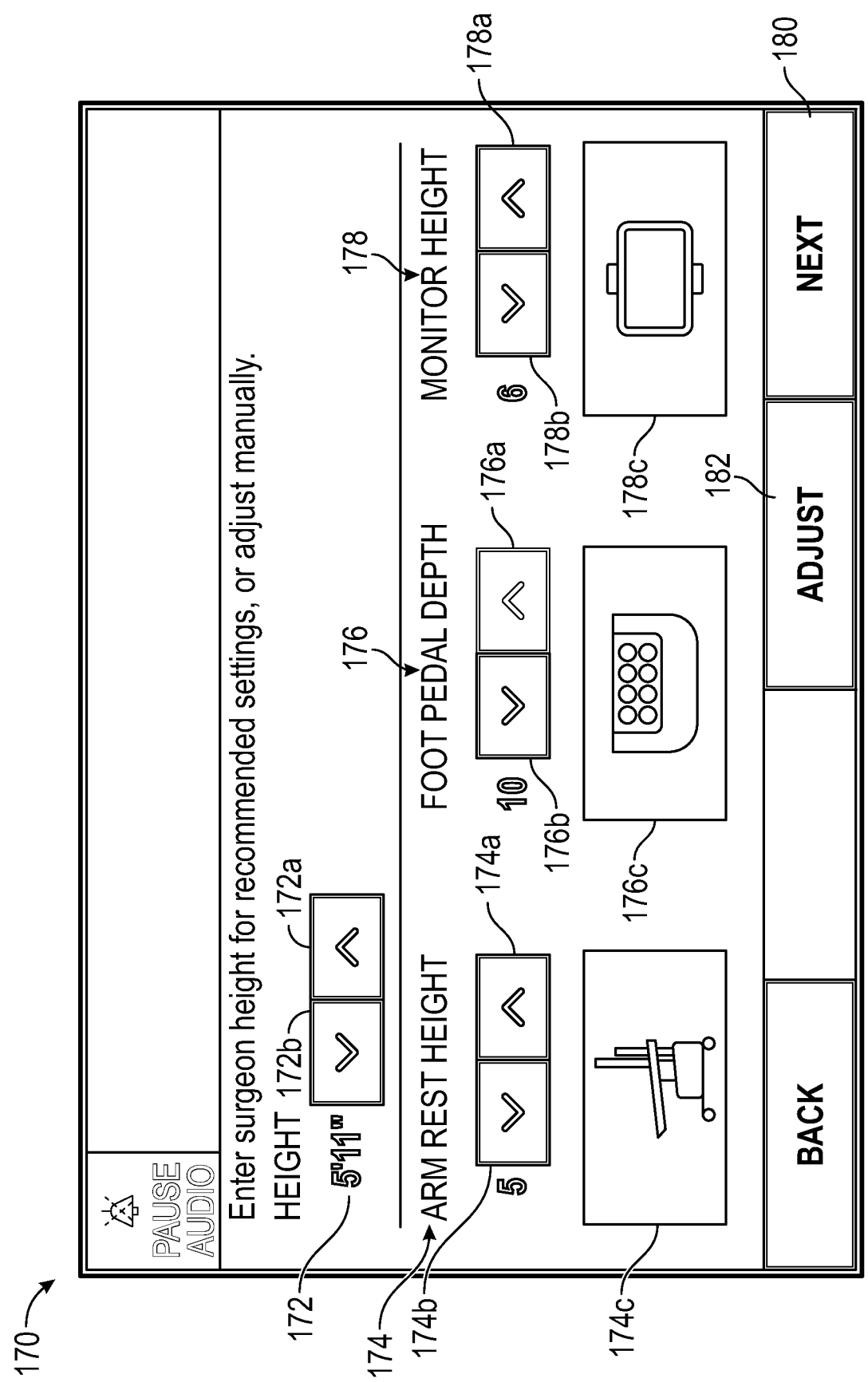
FIG. 18 is a graphical user interface for adjusting ergonomic parameters of the surgical console according to an embodiment of the present disclosure.

Each of the ergonomic parameters may be adjusted during initialization of the surgical console 30, e.g., following calibration of the surgical console 30. With reference to FIG. 18, a user interface 170 for configuring the surgical console 30 is displayed on the first display 32. The clinician can enter his/her height through a clinician height adjustment input 172 using up and down arrows 172a and 172b, respectively. The computer 31 of the surgical console 30 includes a look up table, which is used by the computer 31 to set each of the ergonomic parameters to recommended parameters from the look up table based on the entered height. In particular, for a particular height range, the look up table stores each of the ergonomic parameters, which the computer 31 then utilizes to automatically calculate and/or adjust one or more of the following ergonomic parameters: the height of the first display 32, the height of the armrest 33, and the depth of the foot pedals 36. In embodiments, the user interface 170 may also include physical buttons (not shown) for adjusting each of the ergonomic parameters. The buttons may be disposed on armrest 33.

The clinician may also change each of the ergonomic parameters manually. The user interface 170 includes an armrest height adjustment input 174, a foot pedal depth adjustment input 176, and a display height adjustment input 178. Each of the adjustment inputs 174, 176, 178 includes an up arrow 174a, 176a, 178a, a down arrow 174b, 176b, 178b, and a graphical representation 174c, 176c, 178c of the armrest 33, the foot pedals 36, and the display 32, respectively. The clinician may adjust each of the adjustment inputs 174, 176, 178.

The ergonomic parameters may be expressed on a 0-10 scale or any other suitable range. During adjustment, when a value has reached a low or high limit, the corresponding button (e.g., an up arrow 174a, 176a, 178a or a down arrow 174b, 176b, 178b) to adjust higher or lower is grayed out or is otherwise disabled, where any input (e.g., touch) has no effect on the ergonomic parameter. The user interface 170 also includes a next button 180 and an adjust button 182. The next button 180 is initially available to touch if the clinician does not adjust any settings. Once the clinician adjusts a setting, the next button 180 becomes disabled and the clinician touches the adjust button 182, such that the surgical console 30 can make the inputted adjustments. Similarly, if the computer 31 is used to automatically calculate the ergonomic parameters, pressing the adjust button 182 initiates automatic adjustment of the surgical console 30 but the computer 31.

It will be understood that various modifications may be made to the embodiments disclosed herein. In embodiments, the sensors may be disposed on any suitable portion of the robotic arm. Therefore, the above description should not be construed as limiting, but merely as exemplifications of various embodiments. Those skilled in the art will envision other modifications within the scope and spirit of the claims appended thereto.

What is claimed is:

1. A surgical robotic system comprising:
a surgical table;
a plurality of movable carts being oriented toward the surgical table, each of which includes a robotic arm, and an alignment unit configured to determine an orientation of each of the robotic arms relative to the surgical table; and
a computer coupled to each of the plurality of movable carts and configured to:
calculate a yaw angle for each of the robotic arms; and
output a user interface having a surgical table representation and a graphical representation for each of the robotic arms, wherein the graphical representation for each of the robotic arms displays the calculated yaw angle.

2. The surgical robotic system according to claim 1, wherein each of the robotic arms is aligned based on an alignment pattern projected by the alignment unit onto a surface.

3. The surgical robotic system according to claim 2, wherein the computer is configured to set a state of each of the robotic arms to an aligned state in response to a confirmation from the alignment unit.

4. The surgical robotic system according to claim 3, wherein each of the plurality of movable carts includes a plurality of wheels and a plurality of brakes.

5. The surgical robotic system according to claim 4, wherein each of the plurality of movable carts includes a cart controller configured to identify a corresponding movable cart as registered in response to the plurality of brakes being engaged, the corresponding movable cart being aligned, and the robotic arm being docked to an access port.

6. The surgical robotic system according to claim 5, wherein the cart controller is configured to identify the corresponding movable cart as unregistered in response to at least one of the plurality of brakes being disengaged or the robotic arm being undocked from the access port.

7. The surgical robotic system according to claim 1, wherein the computer is configured to determine whether two adjacent robotic arms are spaced apart by a predetermined distance based on a difference between yaw angles of the two adjacent robotic arms.

8. A method of aligning a robotic arm with a surgical table, the method comprising:
placing a plurality of movable carts around a surgical table, each of the plurality of movable carts includes a robotic arm;
projecting an alignment pattern from an alignment unit onto a surface, the alignment unit is operatively coupled to a movable cart of the plurality of movable carts;
prompting a user to manipulate the alignment pattern by adjusting the alignment unit;
receiving an input indicating that adjustment to the alignment unit is complete;
determining an orientation of the alignment pattern relative to a representative coordinate system;
determining an orientation of each of the robotic arms based on the determined orientation of the alignment pattern;
calculating a yaw angle for each of the robotic arms at a computer coupled to the plurality of movable carts; and
outputting a user interface having a surgical table representation and a graphical representation for each of the robotic arms, wherein the graphical representation for each of the robotic arms displays the calculated yaw angle.

9. The method according to claim 8, wherein projecting the alignment pattern includes projecting at least two portions of the alignment pattern and are configured to indicate an alignment direction.

10. The method according to claim 8, further comprising activating an input device disposed on the alignment unit to confirm that adjustment to the alignment unit is complete.

11. The method according to claim 10, further comprising setting a state of each of the plurality of movable carts to an aligned state in response to a confirmation from the alignment unit.

12. The method according to claim 11, wherein each of the plurality of movable carts includes a plurality of wheels and a plurality of brakes.

13. The method according to claim 12, further comprising identifying a movable cart of the plurality of movable carts as registered in response to the plurality of brakes being engaged, the movable cart being aligned, and the robotic arm being docked to an access port.

14. The method according to claim 13, further comprising identifying the movable cart as unregistered in response to at least one of the plurality of brakes being disengaged or the robotic arm being undocked from the access port.

15. The method according to claim 8, further comprising determining whether two adjacent movable carts of the plurality of the movable carts are spaced apart by a predetermined distance based on a difference between yaw angles of the two adjacent movable carts.

* * * * *